(12) United States Patent
Palti

(10) Patent No.: US 7,912,540 B2
(45) Date of Patent: *Mar. 22, 2011

(54) ARTICLE OF CLOTHING FOR TREATING A TUMOR OR THE LIKE

(75) Inventor: Yoram Palti, Haifa (IL)

(73) Assignee: Standen Ltd., St. Helier (JE)

( * ) Notice: Subject to any disclaimer, the term of this patent is extended or adjusted under 35 U.S.C. 154(b) by 598 days.

This patent is subject to a terminal disclaimer.

(21) Appl. No.: 11/424,141

(22) Filed: Jun. 14, 2006

(65) Prior Publication Data

US 2006/0233867 A1    Oct. 19, 2006

Related U.S. Application Data

(60) Division of application No. 10/285,313, filed on Oct. 31, 2002, now Pat. No. 7,089,054, which is a continuation-in-part of application No. 10/263,329, filed on Oct. 2, 2002, now Pat. No. 7,136,699.

(51) Int. Cl.
*A61N 1/40* (2006.01)
(52) U.S. Cl. .......................................................... 607/2
(58) Field of Classification Search ........................ 607/2
See application file for complete search history.

(56) References Cited

U.S. PATENT DOCUMENTS

| | | | |
|---|---|---|---|
| 2,220,269 A | 11/1940 | Patzold et al. | |
| 3,991,770 A | 11/1976 | LeVeen | |
| 4,016,886 A | 4/1977 | Doss et al. | |
| 4,121,592 A | 10/1978 | Whalley | |
| 4,263,920 A | 4/1981 | Tasto et al. | |
| 4,467,809 A | 8/1984 | Brighton | |
| 4,472,506 A | 9/1984 | Liburdy | |
| 4,622,952 A | 11/1986 | Gordon | |
| 4,626,506 A | 12/1986 | Arnold et al. | |
| 4,676,258 A | 6/1987 | Inokuchi et al. | |
| 4,729,377 A * | 3/1988 | Granek et al. | 600/393 |
| 4,822,470 A | 4/1989 | Chang | |

(Continued)

FOREIGN PATENT DOCUMENTS

EP    0 330 797 A2    9/1989

(Continued)

OTHER PUBLICATIONS

U.S. Appl. No. 11/422,641, filed Jun. 7, 2006, Palti.

(Continued)

*Primary Examiner* — Angela D Sykes
*Assistant Examiner* — Michael Kahelin
(74) *Attorney, Agent, or Firm* — Proskauer

(57) ABSTRACT

An article of clothing is provided for selectively destroying dividing cells in living tissue formed of dividing cells and non-dividing cells. The dividing cells contain polarizable intracellular members and during late anaphase or telophase, the dividing cells are connected to one another by a cleavage furrow. The article of clothing includes insulated electrodes to be coupled to a generator for subjecting the living tissue to electric field conditions sufficient to cause movement of the polarizable intracellular members toward the cleavage furrow in response to a non-homogeneous electric field being induced in the dividing cells. The non-homogeneous electric field produces an increased density electric field in the region of the cleavage furrow. The movement of the polarizable intracellular intracellular members towards the cleavage furrow causes the breakdown thereof which adversely impacts the multiplication of the dividing cells.

16 Claims, 17 Drawing Sheets

U.S. PATENT DOCUMENTS

| | | | |
|---|---|---|---|
| 4,846,178 A | | 7/1989 | Fuxue et al. |
| 4,846,196 A | | 7/1989 | Wiksell et al. |
| 4,923,814 A | | 5/1990 | Marshall |
| 4,936,303 A | | 6/1990 | Detwiler et al. |
| 4,971,991 A | | 11/1990 | Umemura et al. |
| 5,099,756 A | | 3/1992 | Franconi et al. |
| 5,158,071 A | | 10/1992 | Umemura et al. |
| 5,236,410 A | | 8/1993 | Granov et al. |
| 5,269,304 A | | 12/1993 | Matthews |
| 5,312,813 A | | 5/1994 | Costerton et al. |
| 5,386,837 A | | 2/1995 | Sterzer |
| 5,389,069 A | | 2/1995 | Weaver |
| 5,441,532 A | | 8/1995 | Fenn |
| 5,441,746 A | | 8/1995 | Chagnon |
| 5,468,223 A | | 11/1995 | Mir |
| 5,606,971 A | | 3/1997 | Sarvazyan |
| 5,674,267 A | | 10/1997 | Mir et al. |
| 5,718,246 A | | 2/1998 | Vona |
| 5,807,257 A | | 9/1998 | Bridges |
| 5,964,726 A | | 10/1999 | Korenstein et al. |
| 5,976,092 A | | 11/1999 | Chinn |
| 5,984,882 A | | 11/1999 | Rosenschein et al. |
| 6,027,488 A | | 2/2000 | Hofmann et al. |
| 6,043,066 A | | 3/2000 | Mangano et al. |
| 6,055,453 A | | 4/2000 | Hofmann et al. |
| 6,068,650 A | | 5/2000 | Hofmann et al. |
| 6,096,020 A | | 8/2000 | Hofmann |
| 6,319,901 B1 | | 11/2001 | Bernard et al. |
| 6,366,808 B1 | | 4/2002 | Schroeppel et al. |
| 6,413,255 B1 | | 7/2002 | Stern |
| 6,447,499 B2 | | 9/2002 | Gray |
| 6,758,846 B2 * | | 7/2004 | Goble et al. .................... 606/41 |
| 6,856,839 B2 | | 2/2005 | Litovitz |
| 6,868,289 B2 | | 3/2005 | Palti |
| 7,016,725 B2 | | 3/2006 | Palti |
| 2002/0193832 A1 | | 12/2002 | Gray |
| 2002/0193833 A1 | | 12/2002 | Dimmer et al. |
| 2003/0060856 A1 | | 3/2003 | Chornenky et al. |
| 2003/0150372 A1 | | 8/2003 | Palti |
| 2003/0191506 A1 | | 10/2003 | Shloznikov |
| 2004/0176804 A1 | | 9/2004 | Palti |
| 2005/0209640 A1 | | 9/2005 | Palti |
| 2005/0209641 A1 | | 9/2005 | Palti |
| 2005/0209642 A1 | | 9/2005 | Palti |
| 2005/0240173 A1 | | 10/2005 | Palti |
| 2005/0240228 A1 | | 10/2005 | Palti |
| 2006/0149341 A1 | | 7/2006 | Palti |
| 2006/0167499 A1 | | 7/2006 | Palti |

FOREIGN PATENT DOCUMENTS

| | | |
|---|---|---|
| GB | 1 419 660 A1 | 12/1975 |
| GB | 2 026 322 A1 | 2/1980 |
| GB | 2 043 453 A1 | 10/1980 |
| WO | WO 01/60994 | 8/2001 |

OTHER PUBLICATIONS

U.S. Appl. No. 11/422,998, filed Jun. 8, 2006, Palti.

U.S. Appl. No. 11/424,115, filed Jun. 14, 2006, Palti.

U.S. Appl. No. 11/424,001, filed Jun. 14, 2006, Palti.

Hofmann et al., "Electronic Genetic-Physical and Biological Aspects of Cellular Electomanipulation", IEEE Eng. in Med. and Biology Mag., Dec. 1986, p. 6-23, New York.

Berg et al., "Electric Field Effects on Bilogical Membranes:Electoincorporation and Electofusion",Ettore Maj Inter. Science, 1987,p. 135-166,vol. 32,Phys. Science, New York.

Kirson et al., "Disruption of Cancer Cell Replication by Alternating Electric Fields", Cancer Research 64, May 2004, p. 3288-3295, Haifa, Israel.

Asbury et al., "Trapping of DNA in Nonuniform Oscillating Electric Fields", Biophysical Journal, Feb. 1998, p. 1024-1030, vol. 74,Seattle, WA.

* cited by examiner

Cross Section of Isolect With
and Without a Protecting Net

ARTICLE OF CLOTHING FOR TREATING A TUMOR OR THE LIKE

CROSS-REFERENCE TO RELATED APPLICATION

This application is a divisional of U.S. patent application Ser. No. 10/285,313, filed Oct. 31, 2002, which is a continuation-in-part application of U.S. patent application Ser. No. 10/263,329, filed Oct. 2, 2002, each of which is hereby incorporated by reference in its entirety.

TECHNICAL FIELD

This invention concerns selective destruction of rapidly dividing cells in a localized area, and more particularly, to an apparatus and method for selectively destroying dividing cells by applying an electric field having certain prescribed characteristics using an apparatus that is configured to be complimentary to a specific body part.

BACKGROUND

All living organisms proliferate by cell division, including cell cultures, microorganisms (such as bacteria, mycoplasma, yeast, protozoa, and other single-celled organisms), fungi, algae, plant cells, etc. Dividing cells of organisms can be destroyed, or their proliferation controlled, by methods that are based on the sensitivity of the dividing cells of these organisms to certain agents. For example, certain antibiotics stop the multiplication process of bacteria.

The process of eukaryotic cell division is called "mitosis", which involves nice distinct phases (see Darnell et al., Molecular Cell Biology, New York: Scientific American Books, 1986, p. 149). During interphase, the cell replicates chromosomal DNA, which begins condensing in early prophase. At this point, centrioles (each cell contains 2) begin moving towards opposite poles of the cell. In middle prophase, each chromosome is composed of duplicate chromatids. Microtubular spindles radiate from regions adjacent to the centrioles, which are closer to their poles. By late prophase, the centrioles have reached the poles, and some spindle fibers extend to the center of the cell, while others extend from the poles to the chromatids. The cells then move into metaphase, when the chromosomes move toward the equator of the cell and align in the equatorial plane. Next is early anaphase, during which time daughter chromatids separate from each other at the equator by moving along the spindle fibers toward a centromere at opposite poles. The cell begins to elongate along the axis of the pole; the pole-to-pole spindles also elongate. Late anaphase occurs when the daughter chromosomes (as they are not called) each reach their respective opposite poles. At this point, cytokinesis begins as the cleavage furrow begins to form at the equator of the cell. In other words, late anaphase is the point at which pinching the cell membrane begins. During telophase, cytokinesis is nearly complete and spindles disappear. Only a relatively narrow membrane connection joins the two cytoplasms. Finally, the membranes separate fully, cytokinesis is complete and the cell returns to interphase.

In meiosis, the cell undergoes a second division, involving separation of sister chromosomes to opposite poles of the cell along spindle fibers, followed by formation of a cleavage furrow and cell division. However, this division is not preceded by chromosome replication, yielding a haploid germ cell.

Bacteria also divide by chromosome replication, followed by cell separation. However, since the daughter chromosomes separate by attachment to membrane components; there is no visible apparatus that contributes to cell division as in eukaryotic cells.

It is well known that tumors, particularly malignant or cancerous tumors, grow uncontrollably compared to normal tissue. Such expedited growth enables tumors to occupy an ever-increasing space and to damage or destroy tissue adjacent thereto. Furthermore, certain cancers are characterized by an ability to transmit cancerous "seeds", including single cells or small cell clusters (metastases), to new locations where the metastatic cancer cells grow into additional tumors.

The rapid growth of tumors, in general, and malignant tumors in particular, as described above, is the result of relatively frequent cell division or multiplication of these cells compared to normal tissue cells. The distinguishably frequent cell division of cancer cells is the basis for the effectiveness of existing cancer treatments, e.g., irradiation therapy and the use of various chemotherapeutic agents. Such treatments are based on the fact that cells undergoing division are more sensitive to radiation and chemotherapeutic agents than non-dividing cells. Because tumors cells divide much more frequently than normal cells, it is possible, to a certain extent, to selectively damage or destroy tumor cells by radiation therapy and/or chemotherapy. The actual sensitivity of cells to radiation, therapeutic agents, etc., is also dependent on specific characteristics of different types of normal or malignant cell types. Thus, unfortunately, the sensitivity of tumor cells is not sufficiently higher than that many types of normal tissues. This diminishes the ability to distinguish between tumor cells and normal cells, and therefore, existing cancer treatments typically cause significant damage to normal tissues, thus limiting the therapeutic effectiveness of such treatments. Furthermore, the inevitable damage to other tissue renders treatments very traumatic to the patients and, often, patients are unable to recover from a seemingly successful treatment. Also, certain types of tumors are not sensitive at all to existing methods of treatment.

There are also other methods for destroying cells that do not rely on radiation therapy or chemotherapy alone. For example, ultrasonic and electrical methods for destroying tumor cells can be used in addition to or instead of conventional treatments. Electric fields and currents have been used for medical purposes for many years. The most common is the generation of electric currents in a human or animal body by application of an electric field by means of a pair of conductive electrodes between which a potential difference is maintained. These electric currents are used either to exert their specific effects, i.e., to stimulate excitable tissue, or to generate heat by flowing in the body since it acts as a resistor. Examples of the first type of application include the following: cardiac defibrillators, peripheral nerve and muscle stimulators, brain stimulators, etc. Currents are used for heating, for example, in devices for tumor ablation, ablation of malfunctioning cardiac or brain tissue, cauterization, relaxation of muscle rheumatic pain and other pain, etc.

Another use of electric fields for medical purposes involves the utilization of high frequency oscillating fields transmitted from a source that emits an electric wave, such as an RF wave or a microwave source that is directed at the part of the body that is of interest (i.e., target). In these instances, there is no electric energy conduction between the source and the body; but rather, the energy is transmitted to the body by radiation or induction. More specifically, the electric energy generated by the source reaches the vicinity of the body via a conductor and is transmitted from it through air or some other electric insulating material to the human body.

In a conventional electrical method, electrical current is delivered to a region of the target tissue using electrodes that are placed in contact with the body of the patient. The applied electrical current destroys substantially all cells in the vicinity of the target tissue. Thus, this type of electrical method does not discriminate between different types of cells within the target tissue and results in the destruction of both tumor cells and normal cells.

Electric fields that can be used in medical applications can thus be separated generally into two different modes. In the first mode, the electric fields are applied to the body or tissues by means of conducting electrodes. These electric fields can be separated into two types, namely (1) steady fields or fields that change at relatively slow rates, and alternating fields of low frequencies that induce corresponding electric currents in the body or tissues, and (2) high frequency alternating fields (above 1 MHz) applied to the body by means of the conducting electrodes. In the second mode, the electric fields are high frequency alternating fields applied to the body by means of insulated electrodes.

The first type of electric field is used, for example, to stimulate nerves and muscles, pace the heart, etc. In fact, such fields are used in nature to propagate signals in nerve and muscle fibers, central nervous system (CNS), heart, etc. The recording of such natural fields is the basis for the ECG, EEG, EMG, ERG, etc. The field strength in these applications, assuming a medium of homogenous electric properties, is simply the voltage applied to the stimulating/recording electrodes divided by the distance between them. These currents can be calculated by Ohm's law and can have dangerous stimulatory effects on the heart and CNS and can result in potentially harmful ion concentration changes. Also, if the currents are strong enough, they can cause excessive heating in the tissues. This heating can be calculated by the power dissipated in the tissue (the product of the voltage and the current).

When such electric fields and currents are alternating, their stimulatory power, on nerve, muscle, etc., is an inverse function of the frequency. At frequencies above 1-10 KHz, the stimulation power of the fields approaches zero. This limitation is due to the fact that excitation induced by electric stimulation is normally mediated by membrane potential changes, the rate of which is limited by the RC properties (time constants on the order of 1 ms) of the membrane.

Regardless of the frequency, when such current inducing fields are applied, they are associated with harmful side effects caused by currents. For example, one negative effect is the changes in ionic concentration in the various "compartments" within the system, and the harmful products of the electrolysis taking place at the electrodes, or the medium in which the tissues are imbedded. The changes in ion concentrations occur whenever the system includes two or more compartments between which the organism maintains ion concentration differences. For example, for most tissues, $[Ca^{++}]$ in the extracellular fluid is about $2 \times 10^{-3}$ M, while in the cytoplasm of typical cells its concentration can be as low as $10^{-7}$ M. A current induced in such a system by a pair of electrodes, flows in part from the extracellular fluid into the cells and out again into the extracellular medium. About 2% of the current flowing into the cells is carried by the $Ca^{++}$ ions. In contrast, because the concentration of intracellular $Ca^{++}$ is much smaller, only a negligible fraction of the currents that exits the cells is carried by these ions. Thus, $Ca^{++}$ ions accumulate in the cells such that their concentrations in the cells increases, while the concentration in the extracellular compartment may decrease. These effects are observed for both DC and alternating currents (AC). The rate of accumulation of the ions depends on the current intensity ion mobilities, membrane ion conductance, etc. An increase in $[Ca^{++}]$ is harmful to most cells and if sufficiently high will lead to the destruction of the cells. Similar considerations apply to other ions. In view of the above observations, long term current application to living organisms or tissues can result in significant damage. Another major problem that is associated with such electric fields, is due to the electrolysis process that takes place at the electrode surfaces. Here charges are transferred between the metal (electrons) and the electrolytic solution (ions) such that charged active radicals are formed. These can cause significant damage to organic molecules, especially macromolecules and thus damage the living cells and tissues.

In contrast, when high frequency electric fields, above 1 MHz and usually in practice in the range of GHz, are induced in tissues by means of insulated electrodes, the situation is quite different. These type of fields generate only capacitive or displacement currents, rather than the conventional charge conducting currents. Under the effect of this type of field, living tissues behave mostly according to their dielectric properties rather than their electric conductive properties. Therefore, the dominant field effect is that due to dielectric losses and heating. Thus, it is widely accepted that in practice, the meaningful effects of such fields on living organisms, are only those due to their heating effects, i.e., due to dielectric losses.

In U.S. Pat. No. 6,043,066 ('066) to Mangano, a method and device are presented which enable discrete objects having a conducting inner core, surrounded by a dielectric membrane to be selectively inactivated by electric fields via irreversible breakdown of their dielectric membrane. One potential application for this is in the selection and purging of certain biological cells in a suspension. According to the '066 patent, an electric field is applied for targeting selected cells to cause breakdown of the dielectric membranes of these tumor cells, while purportedly not adversely affecting other desired subpopulations of cells. The cells are selected on the basis of intrinsic or induced differences in a characteristic electroporation threshold. The differences in this threshold can depend upon a number of parameters, including the difference in cell size.

The method of the '066 patent is therefore based on the assumption that the electroporation threshold of tumor cells is sufficiently distinguishable from that of normal cells because of differences in cell size and differences in the dielectric properties of the cell membranes. Based upon this assumption, the larger size of many types of tumor cells makes these cells more susceptible to electroporation and thus, it may be possible to selectively damage only the larger tumor cell membranes by applying an appropriate electric field. One disadvantage of this method is that the ability to discriminate is highly dependent upon cell type, for example, the size difference between normal cells and tumor cells is significant only in certain types of cells. Another drawback of this method is that the voltages which are applied can damage some of the normal cells and may not damage all of the tumor cells because the differences in size and membrane dielectric properties are largely statistical and the actual cell geometries and dielectric properties can vary significantly.

What is needed in the art and has heretofore not been available is an apparatus for destroying dividing cells, wherein the apparatus better discriminates between dividing cells, including single-celled organisms, and non-dividing cells and is capable of selectively destroying the dividing cells or organisms with substantially no affect on the non-dividing cells or organisms and which can be configured to applied to a specific body part, such as an extremity and thus lends itself to being incorporated into an article of clothing.

SUMMARY

An apparatus for use in a number of different applications for selectively destroying cells undergoing growth and division is provided. This includes, cell, particularly tumor cells, in living tissue and single-celled organisms. The apparatus can be incorporated into a number of different configurations that are specifically designed to be effective for specific body parts so that the apparatus distinctly targets a localized area to eliminate or control the growth of such living tissue or organisms. For example and as will be described in greater detail hereinafter, the apparatus is particularly capable of being incorporated into a piece of clothing that is worn over the tumor area. One of the configurations of the apparatus is in the form of a hat, cap or other type of structure to be fitted over a person's head for treating intra-cranial tumors, external scalp lesions or other lesions. In another configuration, the apparatus is in the form of a modified bra or the like to be fitted over breasts for treating breast cancer or other type of tumor condition. In addition, the apparatus can be incorporated into clothing that is to be worn over other body parts, such as testicles, a hand, leg, arm, neck, etc., for treating a localized tumor in one of these locations (body parts). For example, a high standing collar member or necklace type structure can be used to treat thyroid, parathyroid, laryngeal lesions, etc. In this embodiment, the apparatus (either completely or partially) is disposed within clothing that is fit around the neck for treating these conditions. In another aspect, localized treatment is provided by the apparatus when it is in the form of an internal member (e.g., a probe or catheter) that is inserted into the body through a natural pathway, such as the urethra, vagina, etc., or the member can penetrate the skin to and other tissues to reach an internal target.

A major use of the present apparatus is in the treatment of tumors by selective destruction of tumor cells with substantially no affect on normal tissue cells, and thus, the exemplary apparatus is described below in the context of selective destruction of tumor cells. It should be appreciated however, that for purpose of the following description, the term "cell" may also refer to a single-celled organism (eubacteria, bacteria, yeast, protozoa), multi-celled organisms (fungi, algae, mold), and plants as or parts thereof that are not normally classified as "cells". The exemplary apparatus enables selective destruction of cells undergoing division in a way that is more effective and more accurate (e.g., more adaptable to be aimed at specific targets) than existing methods. Further, the present apparatus causes minimal damage, if any, to normal tissue and, thus, reduces or eliminates many side-effects associated with existing selective destruction methods, such as radiation therapy and chemotherapy. The selective destruction of dividing cells using the present apparatus does not depend on the sensitivity of the cells to chemical agents or radiation. Instead, the selective destruction of dividing cells is based on distinguishable geometrical characteristics of cells undergoing division, in comparison to non-dividing cells, regardless of the cell geometry of the type of cells being treated.

According to one exemplary embodiment, cell geometry-dependent selective destruction of living tissue is performed by inducing a non-homogenous electric field in the cells using an electronic apparatus.

It has been observed by the present inventor that, while different cells in their non-dividing state may have different shapes, e.g., spherical, ellipsoidal, cylindrical, "pancake-like", etc., the division process of practically all cells is characterized by development of a "cleavage furrow" in late anaphase and telophase. This cleavage furrow is a slow constriction of the cell membrane (between the two sets of daughter chromosomes) which appears microscopically as a growing cleft (e.g., a groove or notch) that gradually separates the cell into two new cells. During the division process, there is a transient period (telophase) during which the cell structure is basically that of two sub-cells interconnected by a narrow "bridge" formed of the cell material. The division process is completed when the "bridge" between the two sub-cells is broken. The selective destruction of tumor cells using the present electronic apparatus utilizes this unique geometrical feature of dividing cells.

When a cell or a group of cells are under natural conditions or environment, i.e., part of a living tissue, they are disposed surrounded by a conductive environment consisting mostly of an electrolytic inter-cellular fluid and other cells that are composed mostly of an electrolytic intra-cellular liquid. When an electric field is induced in the living tissue, by applying an electric potential across the tissue; an electric field is formed in the tissue and the specific distribution and configuration of the electric field lines defines the direction of charge displacement, or paths of electric currents in the tissue, if currents are in fact induced in the tissue. The distribution and configuration of the electric field is dependent on various parameters of the tissue, including the geometry and the electric properties of the different tissue components, and the relative conductivities, capacities and dielectric constants (that may be frequency dependent) of the tissue components.

The electric current flow pattern for cells undergoing division is very different and unique as compared to non-dividing cells. Such cells including first and second sub-cells, namely an "original" cell and a newly formed cell, that are connected by a cytoplasm "bridge" or "neck". The currents penetrate the first sub-cell through part of the membrane ("the current source pole"); however, they do not exit the first sub-cell through a portion of its membrane closer to the opposite pole ("the current sink pole"). Instead, the lines of current flow converge at the neck or cytoplasm bridge, whereby the density of the current flow lines is greatly increased. A corresponding, "mirror image", process that takes place in the second sub-cell, whereby the current flow lines diverge to a lower density configuration as they depart from the bridge, and finally exit the second sub-cell from a part of its membrane closes to the current sink.

When a polarizable object is placed in a non-uniform converging or diverging field, electric forces act on it and pull it towards the higher density electric field lines. In the case of dividing cell, electric forces are exerted in the direction of the cytoplasm bridge between the two cells. Since all intercellular organelles and macromolecules are polarizable, they are all force towards the bridge between the two cells. The field polarity is irrelevant to the direction of the force and, therefore, an alternating electric having specific properties can be used to produce substantially the same effect. It will also be appreciated that the concentrated and inhomogeneous electric field present in or near the bridge or neck portion in itself exerts strong forces on charges and natural dipoles and can lead to the disruption of structures associated with these members.

The movement of the cellular organelles towards the bridge disrupts the cell structure and results in increased pressure in the vicinity of the connecting bridge membrane. This pressure of the organelles on the bridge membrane is expected to break the bridge membrane and, thus, it is expected that the dividing cell will "explode" in response to this pressure. The ability to break the membrane and disrupt other cell structures can be enhanced by applying a pulsating alternating electric field that has a frequency from about 50 KHz to about 500 KHz. When this type of electric field is applied to the tissue, the forces exerted on the intercellular organelles have a "hammering" effect, whereby force pulses (or beats) are applied to the organelles numerous times per second, enhancing the movement of organelles of different sizes and masses towards the bridge (or neck) portion from both of the sub-cells, thereby increasing the probability of breaking the cell membrane at the bridge portion. The forces exerted on the intracellular organelles also affect the organelles themselves and may collapse or break the organelles.

According to one exemplary embodiment, the apparatus for applying the electric field is an electronic apparatus that generates the desired electric signals in the shape of waveforms or trains of pulses. The electronic apparatus includes a generator that generates an alternating voltage waveform at frequencies in the range from about 50 KHz to about 500 KHz. The generator is operatively connected to conductive leads which are connected at their other ends to insulated conductors/electrodes (also referred to as isolects) that are activated by the generated waveforms. The insulated electrodes consist of a conductor in contact with a dielectric (insulating layer) that is in contact with the conductive tissue, thus forming a capacitor. The electric fields that are generated by the present apparatus can be applied in several different modes depending upon the precise treatment application.

In one exemplary embodiment, the electric fields are applied by external insulated electrodes which are incorporated into an article of clothing and which are constructed so that the applied electric fields are of a local type that target a specific, localized area of tissue (e.g., a tumor). This embodiment is designed to treat tumors and lesions that are at or below the skin surface by wearing the article of clothing over the target tissue so that the electric fields generated by the insulated electrodes are directed at the tumors (lesions, etc.).

According to another embodiment, the apparatus is used in an internal type application in that the insulated electrodes are in the form of a probe or catheter etc., that enter the body through natural pathways, such as the urethra or vagina, or are configured to penetrate living tissue, until the insulated electrodes are positioned near the internal target area (e.g., an internal tumor).

Thus, the present apparatus utilizes electric fields that fall into a special intermediate category relative to previous high and low frequency applications in that the present electric fields are bio-effective fields that have no meaningful stimulatory effects and no thermal effects. Advantageously, when non-dividing cells are subjected to these electric fields, there is no effect on the cells; however, the situation is much different when dividing cells are subjected to the present electric fields. Thus, the present electronic apparatus and the generated electric fields target dividing cells, such as tumors or the like, and do not target non-dividing cells that is found around in healthy tissue surrounding the target area. Furthermore, since the present apparatus utilizes insulated electrodes, the above mentioned negative effects, obtained when conductive electrodes are used, i.e., ion concentration changes in the cells and the formation of harmful agents by electrolysis, do not occur with the present apparatus. This is because, in general, no actual transfer of charges takes place between the electrodes and the medium, and there is no charge flow in the medium where the currents are capacitive.

It should be appreciated that the present electronic apparatus can also be used in applications other than treatment of tumors in the living body. In fact, the selective destruction utilizing the present apparatus can be used in conjunction with any organism that proliferates division and multiplication, for example, tissue cultures, microorganisms, such as bacteria, mycoplasma, protozoa, fungi, algae, plant cells, etc. Such organisms divide by the formation of a groove or cleft as described above. As the groove or cleft deepens, a narrow bridge is formed between the two parts of the organism, similar to the bridge formed between the sub-cells of dividing animal cells. Since such organisms are covered by a membrane having a relatively low electric conductivity, similar to an animal cell membrane described above, the electric field lines in a dividing organism converge at the bridge connecting the two parts of the dividing organism. The converging field lines result in electric forces that displace polarizable elements and charges within the dividing organism.

The above, and other objects, features and advantages of the present apparatus will become apparent from the following description read in conjunction with the accompanying drawings, in which like reference numerals designate the same elements.

BRIEF DESCRIPTION OF THE DRAWING FIGURES

FIG. 7 is a cross-sectional illustration of a skin patch incorporating the apparatus of FIG. 5 and for placement on a skin surface for treating a tumor or the like;

FIG. 8 is a cross-sectional illustration of the insulated electrodes implanted within the body for treating a tumor or the like;

FIG. 9 is a cross-sectional illustration of the insulated electrodes implanted within the body for treating a tumor or the like;

FIG. 14 is a cross-sectional view of insulated electrodes incorporated into a hat according to a first embodiment for placement on a head for treating an intra-cranial tumor or the like;

FIG. 17 is a cross-sectional top view of an article of clothing having the insulated electrodes incorporated therein for treating a tumor or the like;

FIG. 19 is a cross-sectional view of a probe according to one embodiment for being disposed internally within the body for treating a tumor or the like.

DETAILED DESCRIPTION OF PREFERRED EMBODIMENTS

Figure 1A:
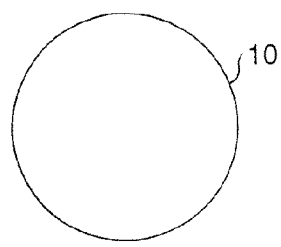
FIGS. 1A-1E are simplified, schematic, cross-sectional, illustrations of various stages of a cell division process.
Figure 1B:
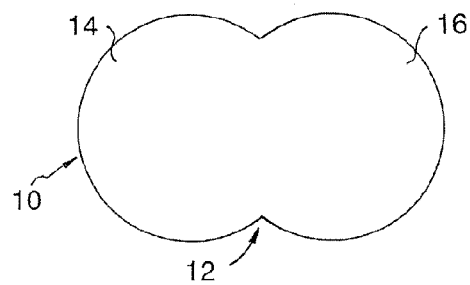
Figure 1C:
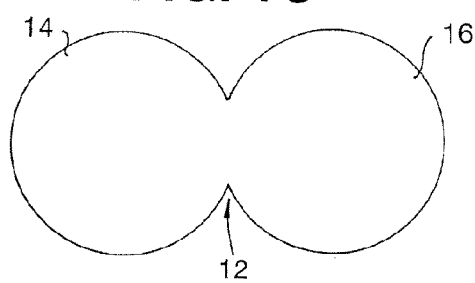
Figure 1D:
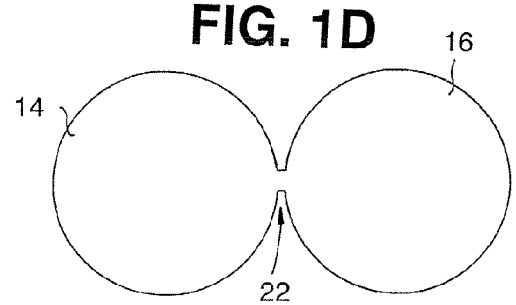

Reference is made to FIGS. 1A-1E which schematically illustrate various stages of a cell division process. FIG. 1A illustrates a cell 10 at its normal geometry, which can be generally spherical (as illustrated in the drawings), ellipsoidal, cylindrical, "pancake-like" or any other cell geometry, as is known in the art. FIGS. 1B-1D illustrate cell 10 during different stages of its division process, which results in the formation of two new cells 18 and 20, shown in FIG. 1E.

Figure 1E:
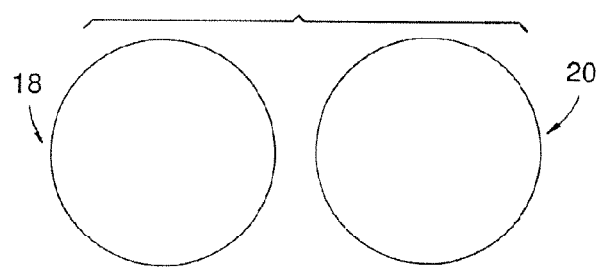

As shown in FIGS. 1B-1D, the division process of cell 10 is characterized by a slowly growing cleft 12 which gradually separates cell 10 into two units, namely sub-cells 14 and 16, which eventually evolve into new cells 18 and 20 (FIG. 1E). A shown specifically in FIG. 1D, the division process is characterized by a transient period during which the structure of cell 10 is basically that of the two sub-cells 14 and 16 interconnected by a narrow "bridge" 22 containing cell material (cytoplasm surrounded by cell membrane).

Figure 2A:
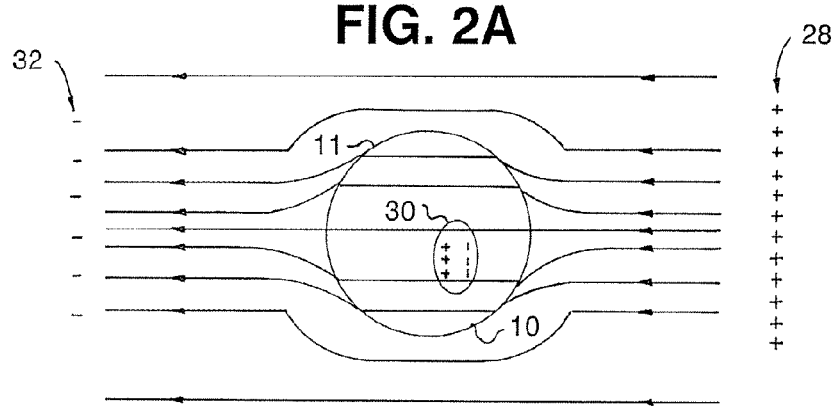
FIGS. 2A and 2B are schematic illustrations of a non-dividing cell being subjected to an electric field.
Figure 2B:
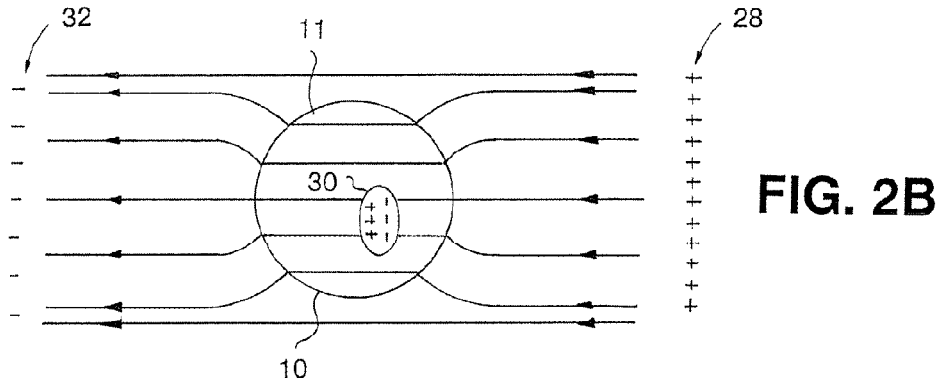

Reference is now made to FIGS. 2A and 2B, which schematically illustrate non-dividing cell 10 being subjected to an electric field produced by applying an alternating electric potential, at a relatively low frequency and at a relatively high frequency, respectively. Cell 10 includes intracellular organelles, e.g., a nucleus 30. Alternating electric potential is applied across electrodes 28 and 32 that can be attached externally to a patient at a predetermined region, e.g., in the vicinity of the tumor being treated. When cell 10 is under natural conditions, i.e., part of a living tissue, it is disposed in a conductive environment (hereinafter referred to as a "volume conductor") consisting mostly of electrolytic inter-cellular liquid. When an electric potential is applied across electrodes 28 and 32, some of the field lines of the resultant electric field (or the current induced in the tissue in response to the electric field) penetrate the cell 10, while the rest of the field lines (or induced current) flow in the surrounding medium. The specific distribution of the electric field lines, which is substantially consistent with the direction of current flow in this instance, depends on the geometry and the electric properties of the system components, e.g., the relative conductivities and dielectric constants of the system components, that can be frequency dependent. For low frequencies, e.g., frequencies lower than 10 KHz, the conductance properties of the components completely dominate the current flow and the field distribution, and the field distribution is generally as depicted in FIG. 2A. At higher frequencies, e.g., at frequencies of between 10 KHz and 1 MHz, the dielectric properties of the components becomes more significant and eventually dominate the field distribution, resulting in field distribution lines as depicted generally in FIG. 2B.

For constant (i.e., DC) electric fields or relatively low frequency alternating electric fields, for example, frequencies under 10 KHz, the dielectric properties of the various components are not significant in determining and computing the field distribution. Therefore, as a first approximation, with regard to the electric field distribution, the system can be reasonably represented by the relative impedances of its various components. Using this approximation, the intercellular (i.e., extracellular) fluid and the intracellular fluid each has a relatively low impedance, while the cell membrane 11 has a relatively high impedance. Thus, under low frequency conditions, only a fraction of the electric field lines (or currents induced by the electric field) penetrate membrane 11 of the cell 10. At relatively high frequencies (e.g., 10 KHz-1 MHz), in contrast, the impedance of membrane 11 relative to the intercellular and intracellular fluids decreases, and thus, the fraction of currents penetrating the cells increases significantly. It should be noted that at very high frequencies, i.e., above 1 MHz, the membrane capacitance can short the membrane resistance and, therefore, the total membrane resistance can become negligible.

In any of the embodiments described above, the electric field lines (or induced currents) penetrate cell 10 from a portion of the membrane 11 closest to one of the electrodes generating the current, e.g., closest to positive electrode 28 (also referred to herein as "source"). The current flow pattern across cell 10 is generally uniform because, under the above approximation, the field induced inside the cell is substantially homogeneous. The currents exit cell 10 through a portion of membrane 11 closest to the opposite electrode, e.g., negative electrode 32 (also referred to herein as "sink").

The distinction between field lines and current flow can depend on a number of factors, for example, on the frequency of the applied electric potential and on whether electrodes 28 and 32 are electrically insulated. For insulated electrodes applying a DC or low frequency alternating voltage, there is practically no current flow along the lines of the electric field. At higher frequencies, the displacement currents are induced in the tissue due to charging and discharging of the electrode insulation and the cell membranes (which act as capacitors to a certain extent), and such currents follow the lines of the electric field. Fields generated by non-insulated electrodes, in contrast, always generate some form of current flow, specifically, DC or low frequency alternating fields generate conductive current flow along the field lines, and high frequency alternating fields generate both conduction and displacement currents along the field lines. It should be appreciated, however, that movement of polarizable intracellular organelles according to the present invention (as described below) is not dependent on actual flow of current and, therefore, both insulated and non-insulated electrodes can be used efficiently. Several advantages of insulated electrodes are that they have lower power consumption and cause less heating of the treated regions.

According to one exemplary embodiment of the present invention, the electric fields that are used are alternating fields having frequencies that are in the range from about 50 KHz to about 500 KHz, and preferably from about 100 KHz to about 300 KHz. For ease of discussion, these type of electric fields are also referred to below as "TC fields", which is an abbreviation of "Tumor Curing electric fields", since these electric fields fall into an intermediate category (between high and low frequency ranges) that have bio-effective field properties while having no meaningful stimulatory and thermal effects. These frequencies are sufficiently low so that the system behavior is determined by the system's Ohmic (conductive) properties but sufficiently high enough not to have any stimulation effect on excitable tissues. Such a system consists of two types of elements, namely, the intercellular, or extracellular fluid, or medium and the individual cells. The intercellular fluid is mostly an electrolyte with a specific resistance of about 40-100 Ohm*cm. As mentioned above, the cells are characterized by three elements, namely (1) a thin, highly electric resistive membrane that coats the cell; (2) internal cytoplasm that is mostly an electrolyte that contains numerous macromolecules and micro-organelles, including the nucleus; and (3) membranes, similar in their electric properties to the cell membrane, cover the micro-organelles.

When this type of system is subjected to the present TC fields (e.g., alternating electric fields in the frequency range of 100 KHz-300 KHz) most of the lines of the electric field and currents tend away from the cells because of the high resistive cell membrane and therefore the lines remain in the extracellular conductive medium. In the above recited frequency range, the actual fraction of electric field or currents that penetrates the cells is a strong function of the frequency.

FIG. 2 schematically depicts the resulting field distribution in the system. As illustrated, the lines of force, which also depict the lines of potential current flow across the cell volume mostly in parallel with the undistorted lines of force (the main direction of the electric field). In other words, the field inside the cells is mostly homogeneous. In practice, the fraction of the field or current that penetrates the cells is determined by the cell membrane impedance value relative to that of the extracellular fluid. Since the equivalent electric circuit of the cell membrane is that of a resistor and capacitor in parallel, the impedance is a function of the frequency. The higher the frequency, the lower the impedance, the larger the fraction of penetrating current and the smaller the field distortion.

As previously mentioned, when cells are subjected to relatively weak electric fields and currents that alternate at high frequencies, such as the present TC fields having a frequency in the range of 50 KHz-500 KHz, they have no effect on the non-dividing cells. While the present TC fields have no detectable effect on such systems, the situation becomes different in the presence of dividing cells.

Figure 3A:
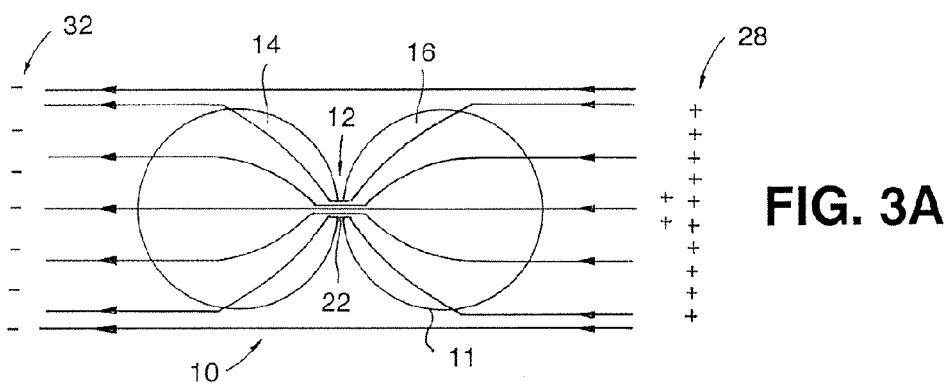
FIGS. 3A, 3B and 3C are schematic illustrations of a dividing cell being subjected to an electric field according to one exemplary embodiment, resulting in destruction of the cell (FIG. 3C) in accordance with one exemplary embodiment.
Figure 3B:
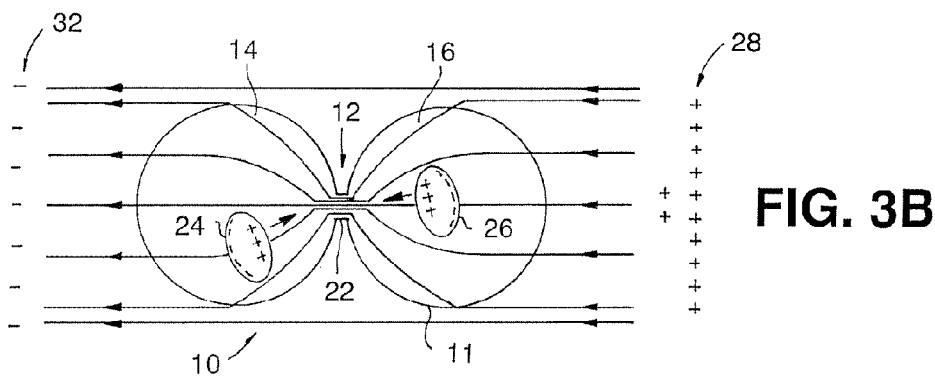
Figure 3C:
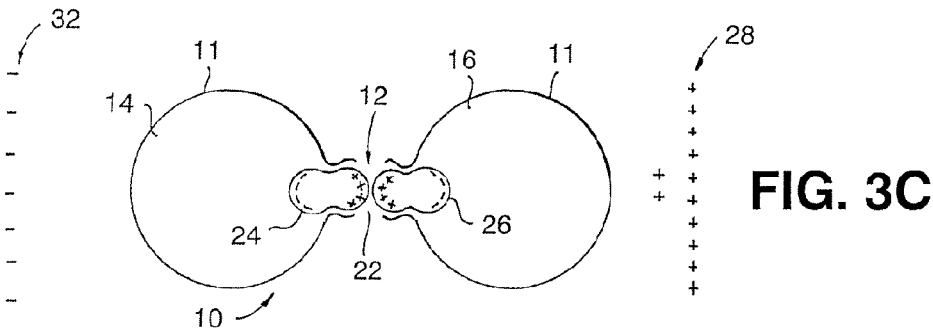

Reference is now made to FIGS. 3A-3C which schematically illustrate the electric current flow pattern in cell 10 during its division process, under the influence of alternating fields (TC fields) in the frequency range from about 100 KHz to about 300 KHz in accordance with one exemplary embodiment. The field lines or induced currents penetrate cell 10 through a part of the membrane of sub-cell 16 closer to electrode 28. However, they do not exit through the cytoplasm bridge 22 that connects sub-cell 16 with the newly formed yet still attached sub-cell 14, or through a part of the membrane in the vicinity of the bridge 22. Instead, the electric field or current flow lines—that are relatively widely separated in sub-cell 16—converge as they approach bridge 22 (also referred to as "neck" 22) and, thus, the current/field line density within neck 22 is increased dramatically. A "mirror image" process takes place in sub-cell 14, whereby the converging field lines in bridge 22 diverge as they approach the exit region of sub-cell 14.

It should be appreciated by persons skilled in the art that homogeneous electric fields do not exert a force on electrically neutral objects, i.e., objects having substantially zero net charge, although such objects can become polarized. However, under a non-uniform, converging electric field, as shown in FIGS. 3A-3C, electric forces are exerted on polarized objects, moving them in the direction of the higher density electric field lines. It will be appreciated that the concentrated electric field that is present in the neck or bridge area in itself exerts strong forces on charges and natural dipoles and can disrupt structures that are associated therewith. One will understand that similar net forces act on charges in an alternating field, again in the direction of the field of higher intensity.

In the configuration of FIGS. 3A and 3B, the direction of movement of polarized and charged objects is towards the higher density electric field lines, i.e., towards the cytoplasm bridge 22 between sub-cells 14 and 16. It is known in the art that all intracellular organelles, for example, nuclei 24 and 26 of sub-cells 14 and 16, respectively, are polarizable and, thus, such intracellular organelles are electrically forced in the direction of the bridge 22. Since the movement is always from lower density currents to the higher density currents, regardless of the field polarity, the forces applied by the alternating electric field to organelles, such as nuclei 24 and 26, are always in the direction of bridge 22. A comprehensive description of such forces and the resulting movement of macromolecules of intracellular organelles, a phenomenon referred to as "dielectrophoresis" is described extensively in literature, e.g., in C. L. Asbury & G. van den Engh, Biophys. J. 74, 1024-1030, 1998, the disclosure of which is hereby incorporated by reference in its entirety.

The movement of the organelles 24 and 26 towards the bridge 22 disrupts the structure of the dividing cell, change the concentration of the various cell constituents and, eventually, the pressure of the converging organelles on bridge membrane 22 results in the breakage of cell membrane 11 at the vicinity of the bridge 22, as shown schematically in FIG. 3C. The ability to break membrane 11 at bridge 22 and to otherwise disrupt the cell structure and organization can be enhanced by applying a pulsating AC electric field, rather than a steady AC field. When a pulsating field is applied, the forces acting on organelles 24 and 26 have a "hammering" effect, whereby pulsed forces beat on the intracellular organelles towards the neck 22 from both sub-cells 14 and 16, thereby increasing the probability of breaking cell membrane 11 in the vicinity of neck 22.

Figure 4:
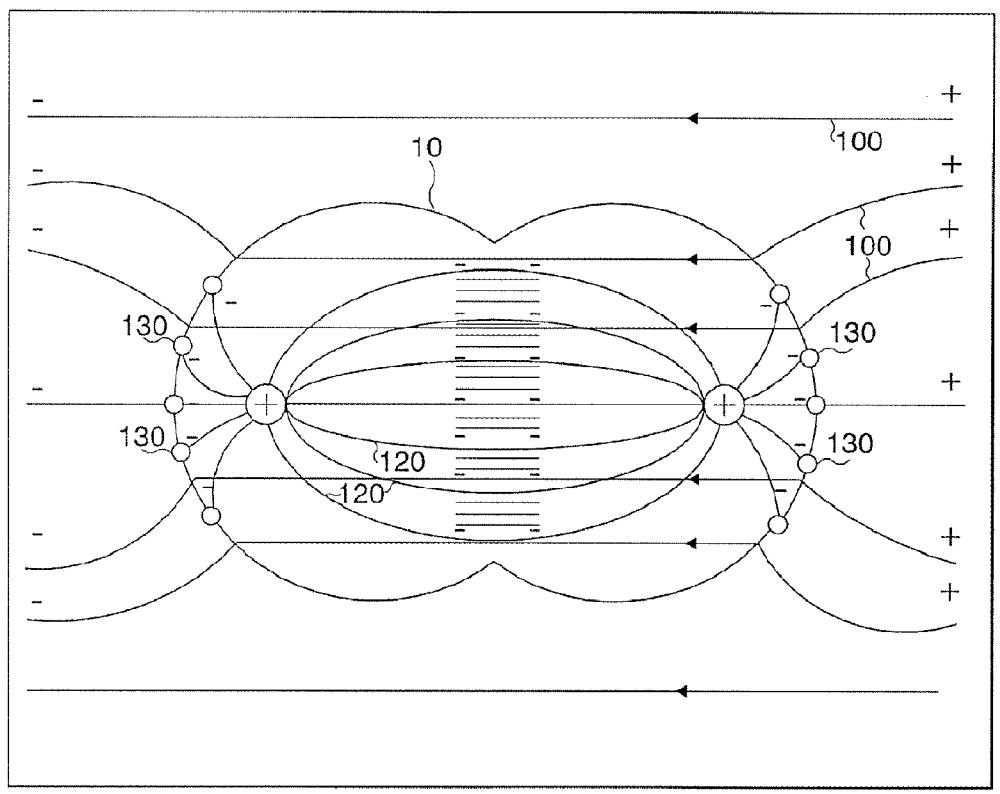
FIG. 4 is a schematic illustration of a dividing cell at one stage being subject to an electric field.

A very important element, which is very susceptible to the special fields that develop within the dividing cells is the microtubule spindle that plays a major role in the division process. In FIG. 4, a dividing cell 10 is illustrated, at an earlier stage as compared to FIGS. 3A and 3B, under the influence of external TC fields (e.g., alternating fields in the frequency range of about 100 KHz to about 300 KHz), generally indicated as lines 100, with a corresponding spindle mechanism generally indicated at 120. The lines 120 are microtubules that are known to have a very strong dipole moment. This strong polarization makes the tubules susceptible to electric fields. Their positive charges are located at the two centrioles while two sets of negative poles are at the center of the dividing cell and the other pair is at the points of attachment of the microtubules to the cell membrane, generally indicated at 130. This structure forms sets of double dipoles and therefore they are susceptible to fields of different directions. It will be understood that the effect of the TC fields on the dipoles does not depend on the formation of the bridge (neck) and thus, the dipoles are influenced by the TC fields prior to the formation of the bridge (neck).

Since the present apparatus (as will be described in greater detail below) utilizes insulated electrodes, the above-mentioned negative effects obtained when conductive electrodes are used, i.e., ion concentration changes in the cells and the formation of harmful agents by electrolysis, do not occur when the present apparatus is used. This is because, in general, no actual transfer of charges takes place between the electrodes and the medium and there is no charge flow in the medium where the currents are capacitive, i.e., are expressed only as rotation of charges, etc.

Figure 5:
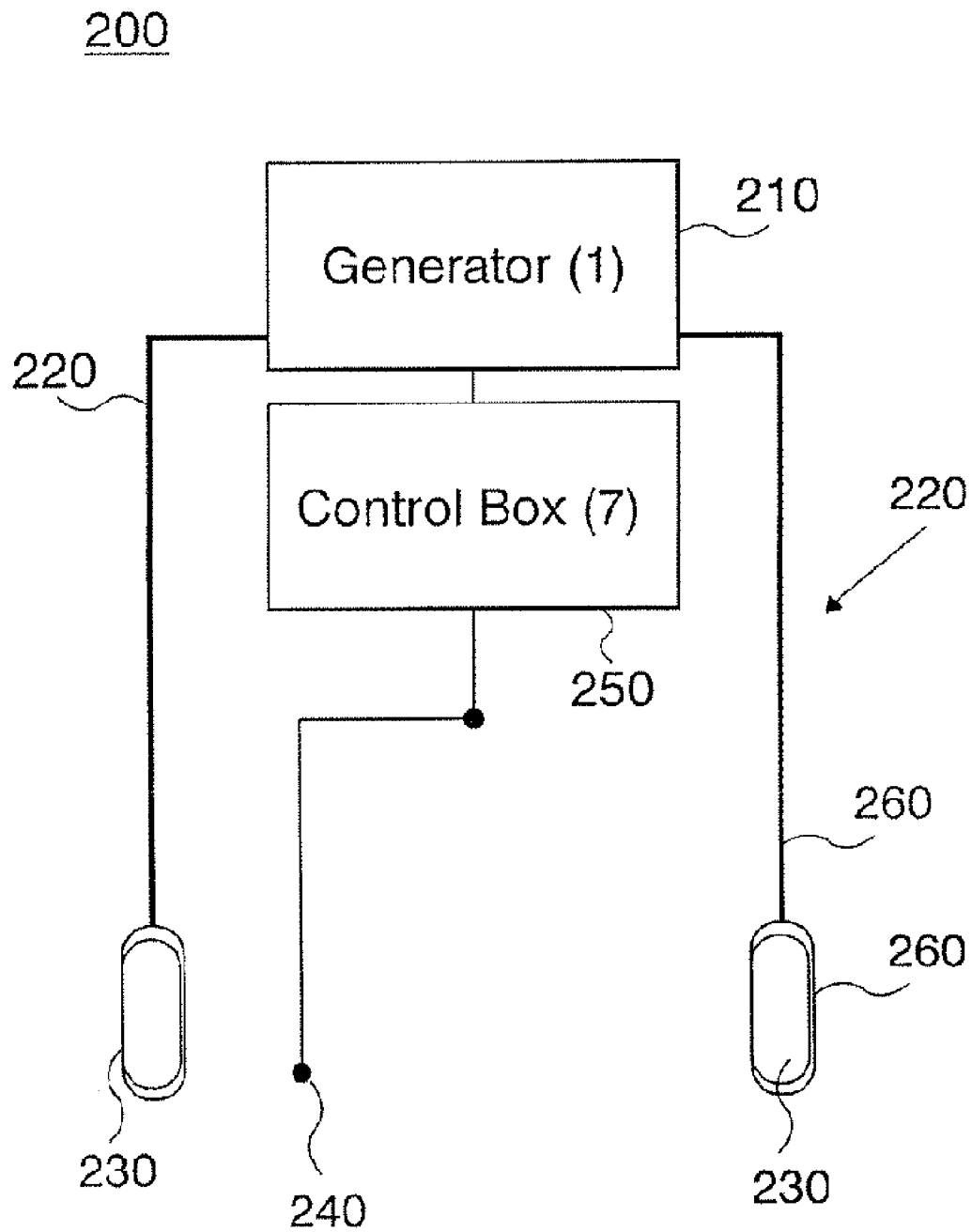
FIG. 5 is a schematic block diagram of an apparatus for applying an electric according to one exemplary embodiment for selectively destroying cells.

Turning now to FIG. 5, the TC fields described above that have been found to advantageously destroy tumor cells are generated by an electronic apparatus 200. FIG. 5 is a simple schematic diagram of the electronic apparatus 200 illustrating the major components thereof. The electronic apparatus 200 generates the desired electric signals (TC signals) in the shape of waveforms or trains of pulses. The apparatus 200 includes a generator 210 and a pair of conductive leads 220 that are attached at one end thereof to the generator 210. The opposite ends of the leads 220 are connected to insulated conductors 230 that are activated by the electric signals (e.g., waveforms). The insulated conductors 230 are also referred to hereinafter as isolects 230. Optionally and according to another exemplary embodiment, the apparatus 200 includes a temperature sensor 240 and a control box 250 which are both added to control the amplitude of the electric field generated so as not to generate excessive heating in the area that is treated.

The generator 210 generates an alternating voltage waveform at frequencies in the range from about 50 KHz to about 500 KHz (preferably from about 100 KHz to about 300 KHz) (i.e., the TC fields). The required voltages are such that the electric field intensity in the tissue to be treated is in the range of about 0.1 V/cm to about 10 V/cm. To achieve this field, the actual potential difference between the two conductors in the isolects 230 is determined by the relative impedances of the system components, as described below.

When the control box 250 is included, it controls the output of the generator 210 so that it will remain constant at the value preset by the user or the control box 250 sets the output at the maximal value that does not cause excessive heating, or the control box 250 issues a warning or the like when the temperature (sensed by temperature sensor 240) exceeds a preset limit.

The leads 220 are standard isolated conductors with a flexible metal shield, preferably grounded so that it prevents the spread of the electric field generated by the leads 220. The isolects 230 have specific shapes and positioning so as to generate an electric field of the desired configuration, direction and intensity at the target volume and only there so as to focus the treatment.

The specifications of the apparatus 200 as a whole and its individual components are largely influenced by the fact that at the frequency of the present TC fields (50 KHz-500 KHz), living systems behave according to their "Ohmic", rather than their dielectric properties. The only elements in the apparatus 200 that behave differently are the insulators of the isolects 230 (see FIGS. 7-9). The isolects 200 consist of a conductor in contact with a dielectric that is in contact with the conductive tissue thus forming a capacitor.

Figure 6:
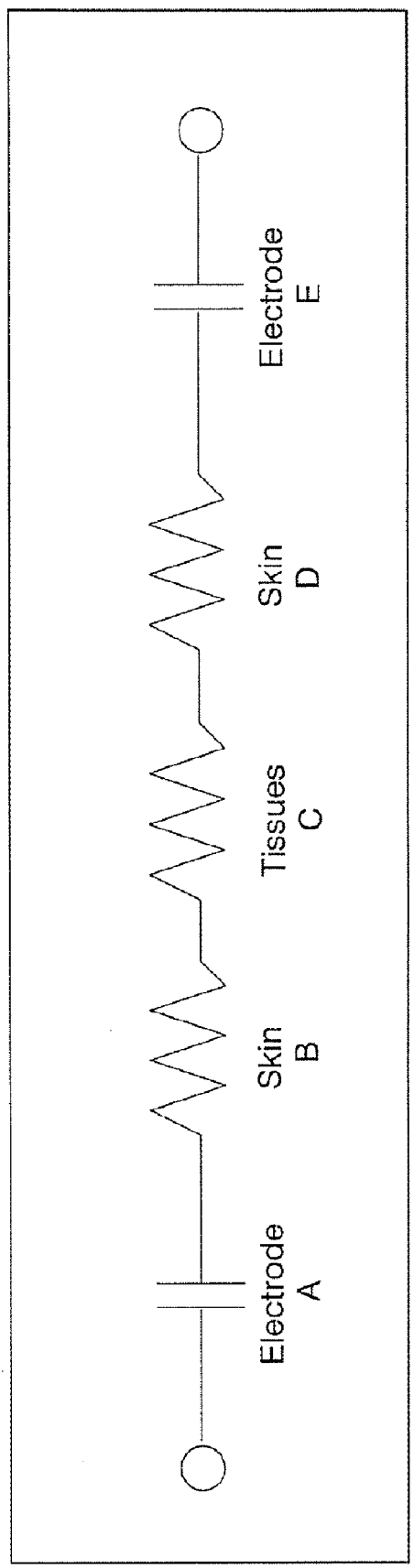
FIG. 6 is a simplified schematic diagram of an equivalent electric circuit of insulated electrodes of the apparatus of FIG. 5.

The details of the construction of the isolects 230 is based on their electric behavior that can be understood from their simplified electric circuit when in contact with tissue as generally illustrated in FIG. 6. In the illustrated arrangement, the potential drop or the electric field distribution between the different components is determined by their relative electric impedance, i.e., the fraction of the field on each component is given by the value of its impedance divided by the total circuit impedance. For example, the potential drop on element? $V_A = A/(A+B+C+D+E)$. Thus, for DC or low frequency AC, practically all the potential drop is on the capacitor (that acts as an insulator). For relatively very high frequencies, the capacitor practically is a short and therefore, practically all the field is distributed in the tissues. At the frequencies of the present TC fields (e.g., 50 KHz to 500 KHz), which are intermediate frequencies, the impedance of the capacitance of the capacitors is dominant and determines the field distribution. Therefore, in order to increase the effective voltage drop across the tissues (field intensity), the impedance of the capacitors is to be decreased (i.e., increase their capacitance). This can be achieved by increasing the effective area of the "plates" of the capacitor, decrease the thickness of the dielectric or use a dielectric with high dielectric constant.

In order to optimize the field distribution, the isolects 230 are configured differently depending upon the application in which the isolects 230 are to be used. There are two principle modes for applying the present electric fields (TC fields). First, the TC fields can be applied by external isolects and second, the TC fields can be applied by internal isolects.

Figure 7:
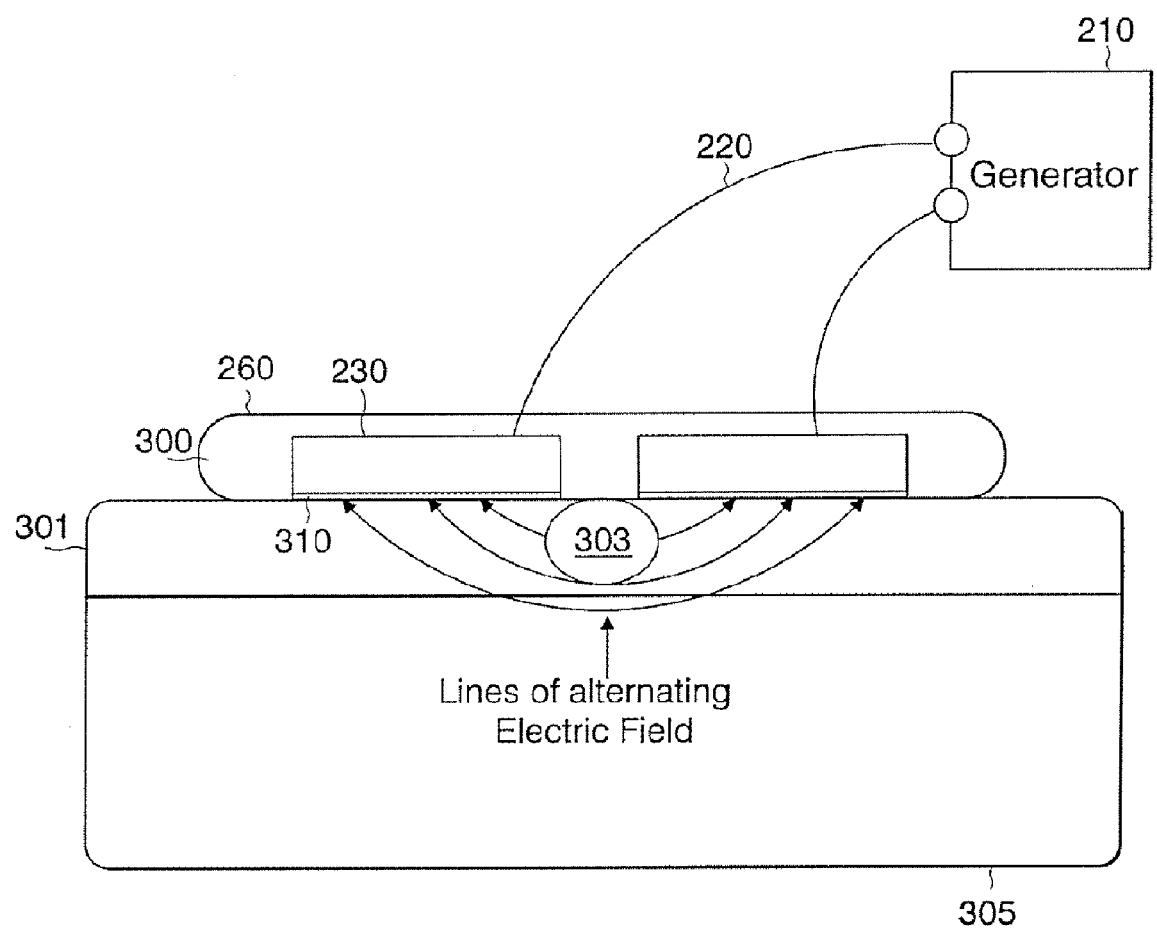

Electric fields (TC fields) that are applied by external isolects can be of a local type or widely distributed type. The first type includes, for example, the treatment of skin tumors and treatment of lesions close to the skin surface. FIG. 7 illustrates an exemplary embodiment where the isolects 230 are incorporated in a skin patch 300. The skin patch 300 can be a self-adhesive flexible patch with one or more pairs of isolects 230. The patch 300 includes internal insulation 310 (formed of a dielectric material) and the external insulation 260 and is applied to skin surface 301 that contains a tumor 303 either on the skin surface 301 or slightly below the skin surface 301. Tissue is generally indicated at 305. To prevent the potential drop across the internal insulation 310 to dominate the system, the internal insulation 310 must have a relatively high capacity. This can be achieved by a large surface area; however, this may not be desired as it will result in the spread of the field over a large area (e.g., an area larger than required to treat the tumor). Alternatively, the internal insulation 310 can be made very thin and/or the internal insulation 310 can be of a high dielectric constant. As the skin resistance between the electrodes (labeled as A and E in FIG. 6) is normally significantly higher than that of the tissue (labeled as C in FIG. 6) underneath it (1-10 KO vs. 0.1-1 KO), most of the potential drop beyond the isolects occurs there. To accommodate for these impedances (Z), the characteristics of the internal insulation 310 (labeled as B and D in FIG. 6) should be such that they have impedance preferably under 100 KO at the frequencies of the present TC fields (e.g., 50 KHz to 500 KHz). For example, if it is desired for the impedance to be about 10 K Ohms or less, such that over 1% of the applied voltage falls on the tissues, for isolects with a surface area of 10 $mm^2$, at frequencies of 200 KHz, the capacity should be on the order of $10^{-10}$ F., which means that using standard insulations with a dielectric constant of 2-3, the thickness of the insulating layer 310 should be about 50-100 microns. An internal field 10 times stronger would be obtained with insulators with a dielectric constant of about 20-50.

Since the thin insulating layer can be very vulnerable, etc., the insulation can be replaced by very high dielectric constant insulating materials, such as titanium dioxide (e.g., rutil), the dielectric constant can reach values of about 200. There a number of different materials that are suitable for use in the intended application and have high dielectric constants. For example, some materials include: lithium nibate ($LiNbO_3$), which is a ferroelectric crystal and has a number of applications in optical, pyroelectric and piezoelectric devices; yttrium iron garnet (YIG) is a ferromagnetic crystal and magneto-optical devices, e.g., optical isolator can be realized from this material; barium titanate ($BaTiO_3$) is a ferromagnetic crystal with a large electro-optic effect; potassium tantalate ($kTaO_3$) which is a dielectric crystal (ferroelectric at low temperature) and has very low microwave loss and tunability of dielectric constant at low temperature; and lithium tantalate ($LiTaO_3$) which is a ferroelectric crystal with similar properties as lithium niobate and has utility in electro-optical, pyroelectric and piezoelectric devices. It will be understood that the aforementioned exemplary materials can be used in combination with the present device where it is desired to use a material having a high dielectric constant.

Figure 10:
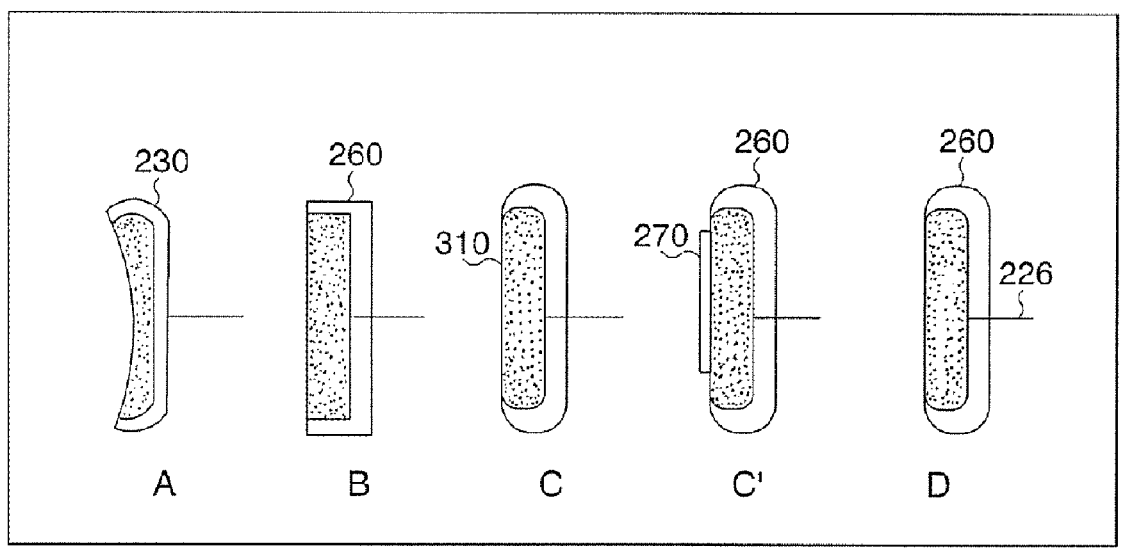
FIGS. 10A-10D are cross-sectional illustrations of various constructions of the insulated electrodes of the apparatus of FIG. 5.

One must also consider another factor that effects the effective capacity of the isolects 230, namely the presence of air between the isolects 230 and the skin. Such presence, which is not easy to prevent, introduces a layer of an insulator with a dielectric constant of 1.0, a factor that significantly lowers the effective capacity of the isolects 230 and neutralizes the advantages of the titanium dioxide (rutil), etc. To overcome this problem, the isolects 230 can be shaped so as to conform with the body structure and/or (2) an intervening filler 270 (as illustrated in FIG. 10C), such as a gel, that has high conductance and a high effective dielectric constant, can be added to the structure. The shaping can be pre-structured (see FIG. 10A) or the system can be made sufficiently flexible so that shaping of the isolects 230 is readily achievable. The gel can be contained in place by having an elevated rim as depicted in FIG. 10C. The gel can be made of hydrogels, gelatins, agar, etc., and can have salts dissolved in it to increase its conductivity. FIGS. 10A-10C illustrate various exemplary configurations for the isolects 230. The exact thickness of the gel is not important so long as it is of sufficient thickness that the gel layer does not dry out during the treatment. In one exemplary embodiment, the thickness of the gel is about 0.5 mm to about 2 mm.

Figure 12:
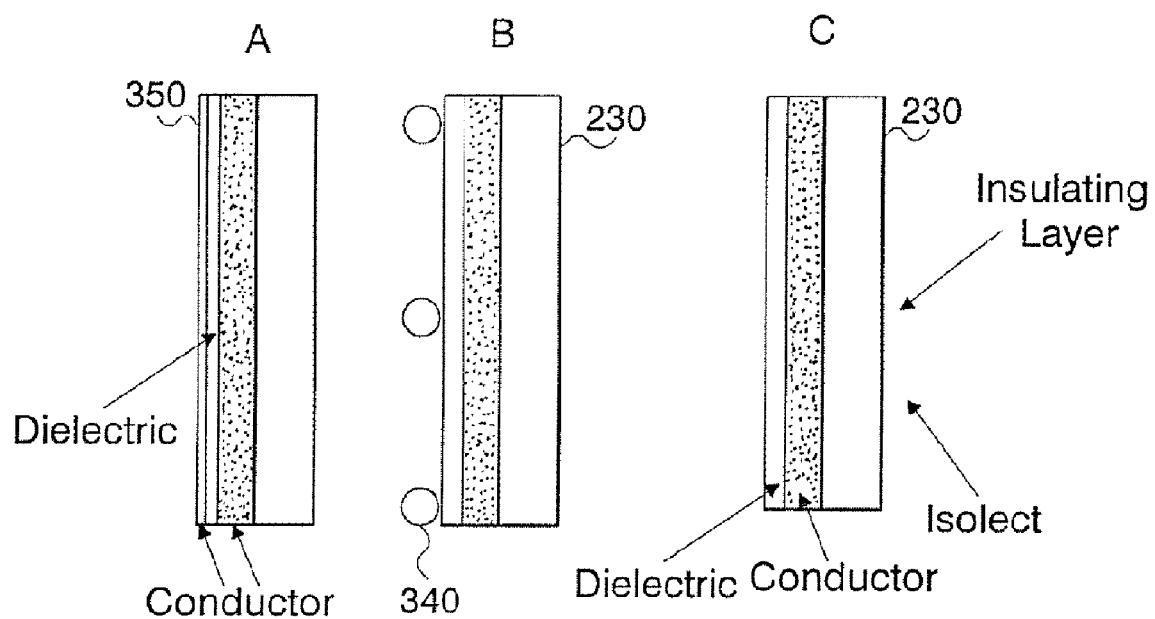
FIGS. 12A-12C are cross-sectional illustrations of various insulated electrodes with and without protective members formed as a part of the construction thereof.

In order to achieve the desirable features of the isolects 230, the dielectric coating of each should be very thin, for example from between 1-50 microns. Since the coating is so thin, the isolects 230 can easily be damaged mechanically. This problem can be overcome by adding a protective feature to the isolect's structure so as to provide desired protection from such damage. For example, the isolect 230 can be coated, for example, with a relatively loose net 340 that prevents access to the surface but has only a minor effect on the effective surface area of the isolect 230 (i.e., the capacity of the isolects 230 (cross section presented in FIG. 12B). The loose net 340 does not effect the capacity and ensures good contact with the skin, etc. The loose net 340 can be formed of a number of different materials; however, in one exemplary embodiment, the net 340 is formed of nylon, polyester, cotton, etc. Alternatively, a very thin conductive coating 350 can be applied to the dielectric portion (insulating layer) of the isolect 230. One exemplary conductive coating is formed of a metal and more particularly of gold. The thickness of the coating 350 depends upon the particular application and also on the type of material used to form the coating 350; however, when gold is used, the coating has a thickness from about 0.1 micron to about 0.1 mm. Furthermore, the rim illustrated in FIG. 10 can also provide some mechanical protection.

However, the capacity is not the only factor to be considered. The following two factors also influence how the isolects 230 are constructed. The dielectric strength of the internal insulating layer 310 and the dielectric losses that occur when it is subjected to the TC field, i.e., the amount of heat generated. The dielectric strength of the internal insulation 310 determines at what field intensity the insulation will be "shorted" and cease to act as an intact insulation. Typically, insulators, such as plastics, have dielectric strength values of about 100V per micron or more. As a high dielectric constant reduces the field within the internal insulator 310, a combination of a high dielectric constant and a high dielectric strength gives a significant advantage. This can be achieved by using a single material that has the desired properties or it can be achieved by a double layer with the correct parameters and thickness. In addition, to further decreasing the possibility that the insulating layer 310 will fail, all sharp edges of the insulating layer 310 should be eliminated as by rounding the corners, etc., as illustrated in FIG. 10D using conventional techniques.

Figure 8:
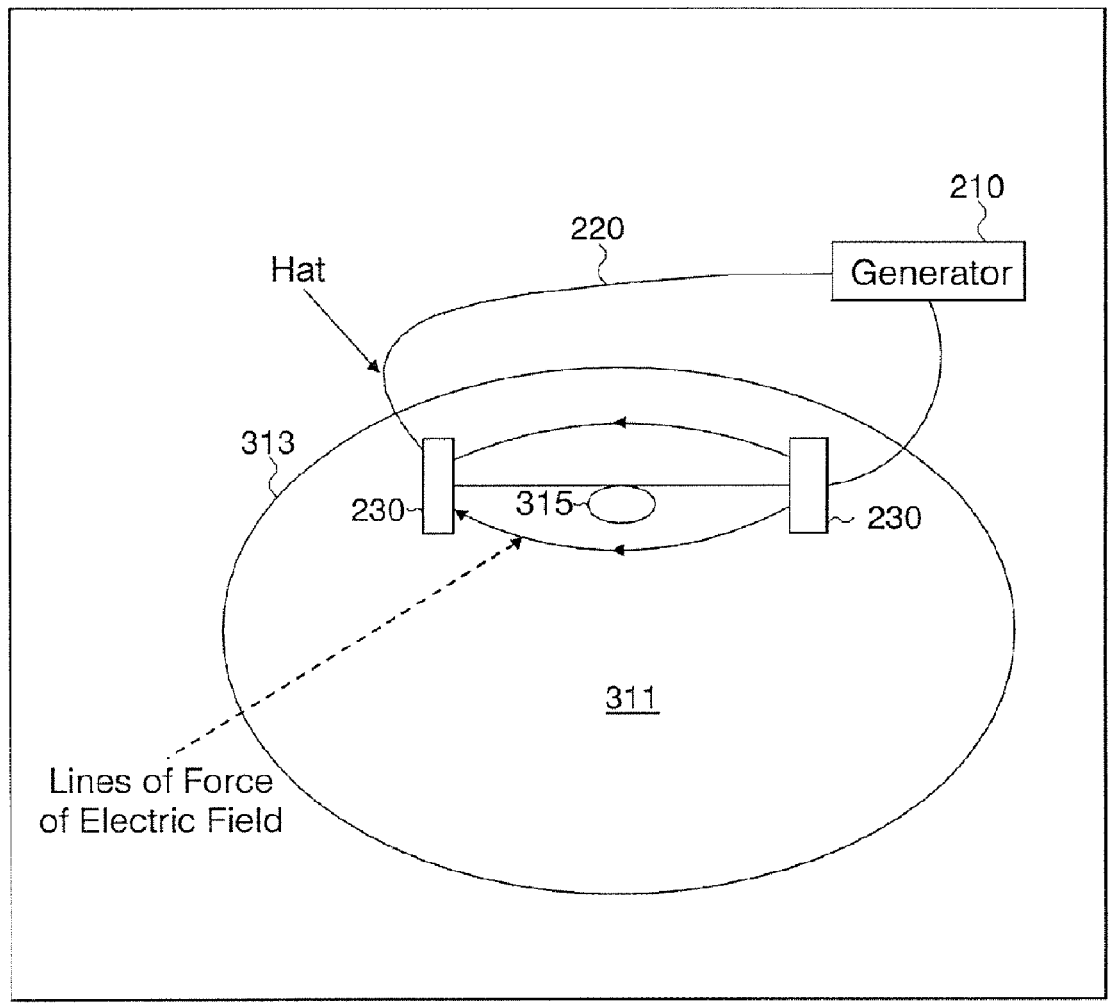
Figure 9:
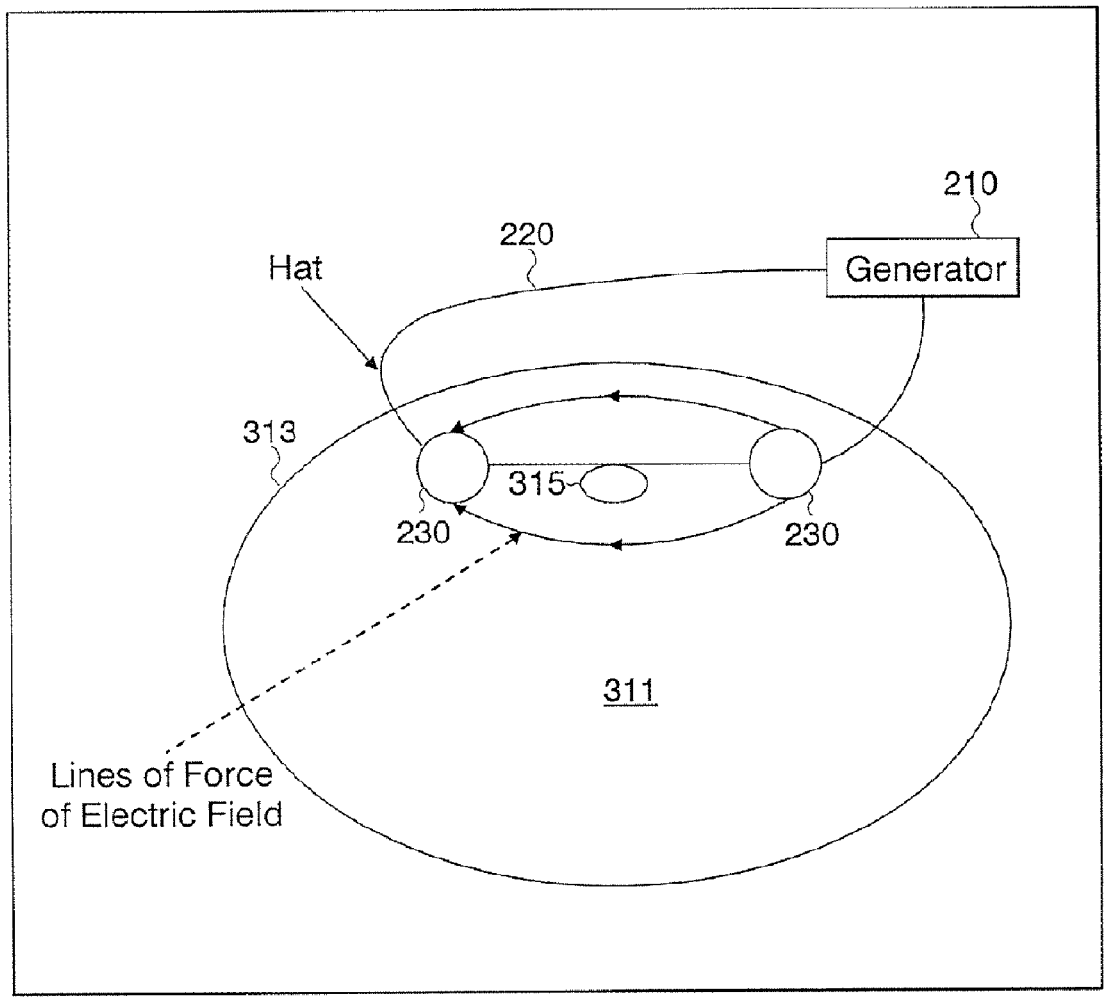

FIGS. 8 and 9 illustrate a second type of treatment using the isolects 230, namely electric field generation by internal isolects 230. A body to which the isolects 230 are implanted is generally indicated at 311 and includes a skin surface 313 and a tumor 315. In this embodiment, the isolects 230 can have the shape of plates, wires or other shapes that can be inserted subcutaneously or a deeper location within the body 311 so as to generate an appropriate field at the target area (tumor 315).

Figure 11:
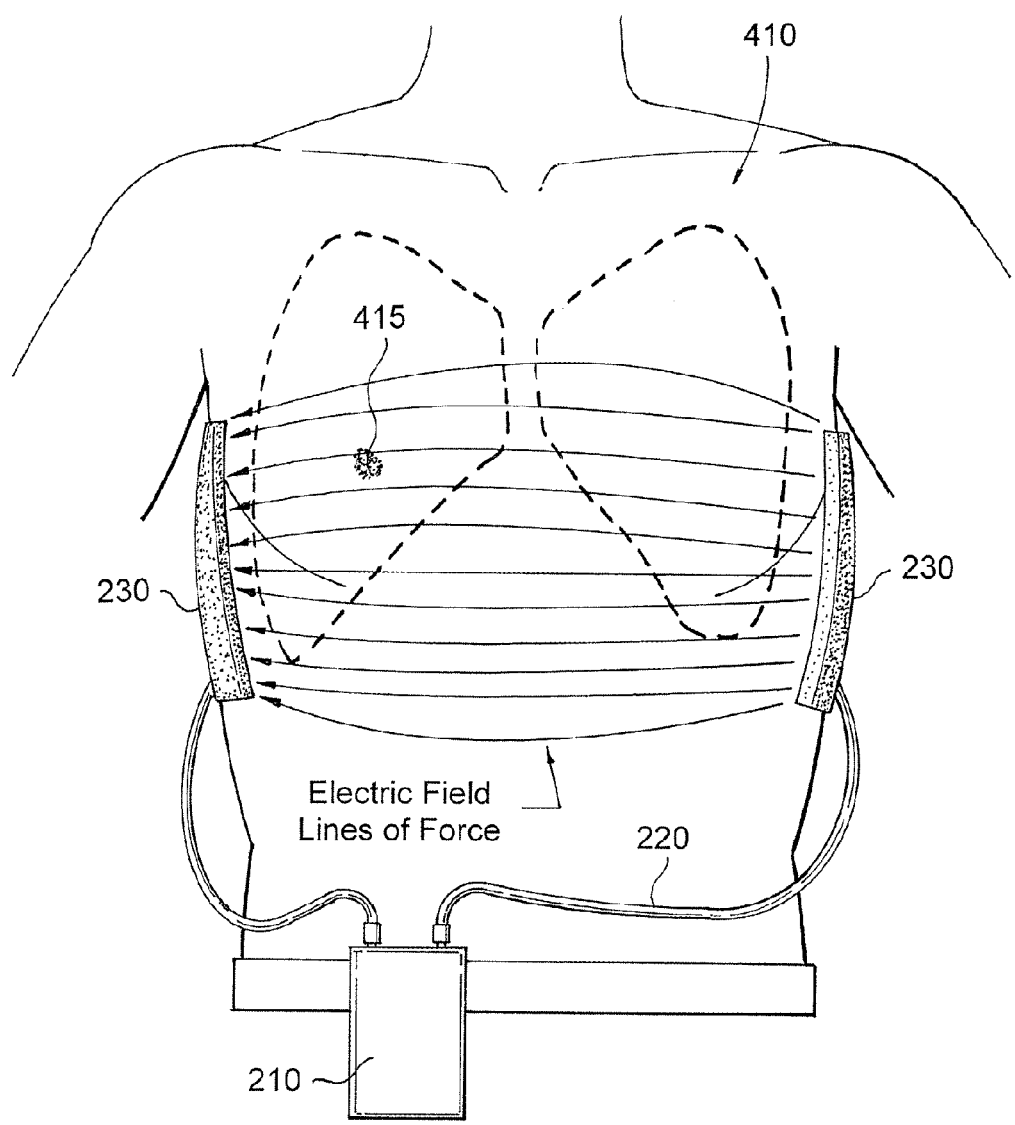
FIG. 11 is a front elevational view in partial cross-section of two insulated electrodes being arranged about a human torso for treatment of a tumor container within the body, e.g., a tumor associated with lung cancer.

It will also be appreciated that the mode of isolects application is not restricted to the above descriptions. In the case of tumors in internal organs, for example, liver, lung, etc., the distance between each member of the pair of isolects 230 can be large. The pairs can even by positioned opposite sides of a torso 410, as illustrated in FIG. 11. The arrangement of the isolects 230 in FIG. 11 is particularly useful for treating a tumor 415 associated with lung cancer or gastrointestinal tumors. In this embodiment, the electric fields (TC fields) spread in a wide fraction of the body.

In order to avoid overheating of the treated tissues, a selection of materials and field parameters is needed. The isolects insulating material should have minimal dielectric losses at the frequency ranges to be used during the treatment process. This factor can be taken into consideration when choosing the particular frequencies for the treatment. The direct heating of the tissues will most likely be dominated by the heating due to current flow (given by the I*R product). In addition, the isolect (insulated electrode) 230 and its surroundings should be made of materials that facilitate heat losses and its general structure should also facilitate head losses, i.e., minimal structures that block heat dissipation to the surroundings (air) as well as high heat conductivity.

Figure 13:
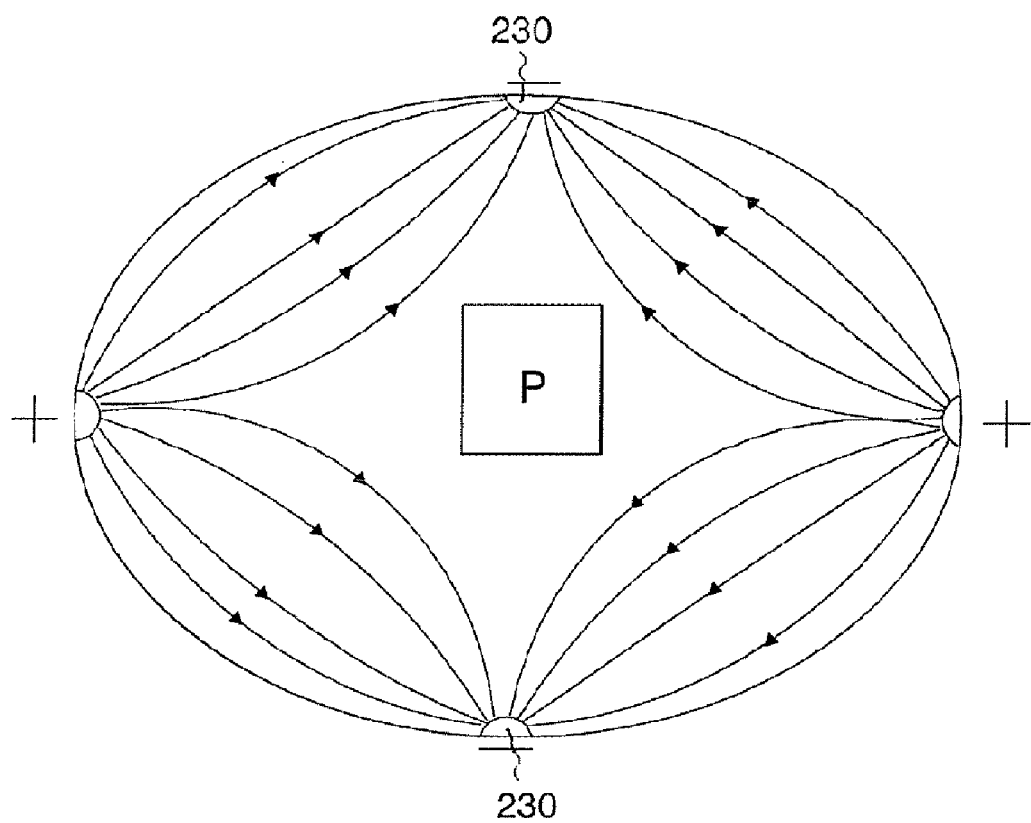
FIG. 13 is a schematic diagram of insulated electrodes that are arranged for focusing the electric field at a desired target while leaving other areas in low field density (i.e., protected areas)

The effectiveness of the treatment can be enhanced by an arrangement of isolects 230 that focuses the field at the desired target while leaving other sensitive areas in low field density (i.e., protected areas). The proper placement of the isolects 230 over the body can be maintained using any number of different techniques, including using a suitable piece of clothing that keeps the isolects at the appropriate positions. FIG. 13 illustrates such an arrangement in which an area labeled as "P" represents a protected area. The lines of field force do not penetrate this protected area and the field there is much smaller than near the isolects 230 where target areas can be located and treated well. In contrast, the field intensity near the four poles is very high.

The following Example serves to illustrate an exemplary application of the present apparatus and application of TC fields; however, this Example is not limiting and does not limit the scope of the present invention in any way.

EXAMPLE

To demonstrate the effectiveness of electric fields having the above described properties (e.g., frequencies between 50 KHz and 500 KHz) in destroying tumor cells, the electric fields were applied to treat mice with malignant melanoma tumors. Two pairs of isolects 230 were positioned over a corresponding pair of malignant melanomas. Only one pair was connected to the generator 210 and 200 KHz alternating electric fields (TC fields) were applied to the tumor for a period of 6 days. One melanoma tumor was not treated so as to permit a comparison between the treated tumor and the non-treated tumor. After treatment for 6 days, the pigmented melanoma tumor remained clearly visible in the non-treated side of the mouse, while, in contrast, no tumor is seen on the treated side of the mouse. The only areas that were visible discernable on the skin were the marks that represented the points of insertion of the isolects 230. The fact that the tumor was eliminated at the treated side was further demonstrated by cutting and inversing the skin so that its inside face was exposed. Such a procedure indicated that the tumor has been substantially, if not completely, eliminated on the treated side of the mouse. The success of the treatment was also further verified by pathhistological examination.

The present inventor has thus uncovered that electric fields having particular properties can be used to destroy dividing cells or tumors when the electric fields are applied to using an electronic device. More specifically, these electric fields fall into a special intermediate category, namely bio-effective fields that have no meaningful stimulatory and no thermal effects, and therefore overcome the disadvantages that were associated with the application of conventional electric fields to a body. It will also be appreciated that the present apparatus can further include a device for rotating the TC field relative to the living tissue. For example and according to one embodiment, the alternating electric potential applies to the tissue being treated is rotated relative to the tissue using conventional devices, such as a mechanical device that upon activation, rotates various components of the present system.

Moreover and according to yet another embodiment, the TC fields are applied to different pairs of the insulated electrodes 230 in a consecutive manner. In other words, the generator 210 and the control system thereof can be arranged so that signals are sent at periodic intervals to select pairs of insulated electrodes 230, thereby causing the generation of the TC fields of different directions by these insulated electrodes 230. Because the signals are sent at select times from the generator to the insulated electrodes 230, the TC fields of changing directions are generated consecutively by different insulated electrodes 230. This arrangement has a number of advantages and is provided in view of the fact that the TC fields have maximal effect when they are parallel to the axis of cell division. Since the orientation of cell division is in most cases random, only a fraction of the dividing cells are affected by any given field. Thus, using fields of two or more orientations increases the effectiveness since it increases the chances that more dividing cells are affected by a given TC field.

Figure 14:
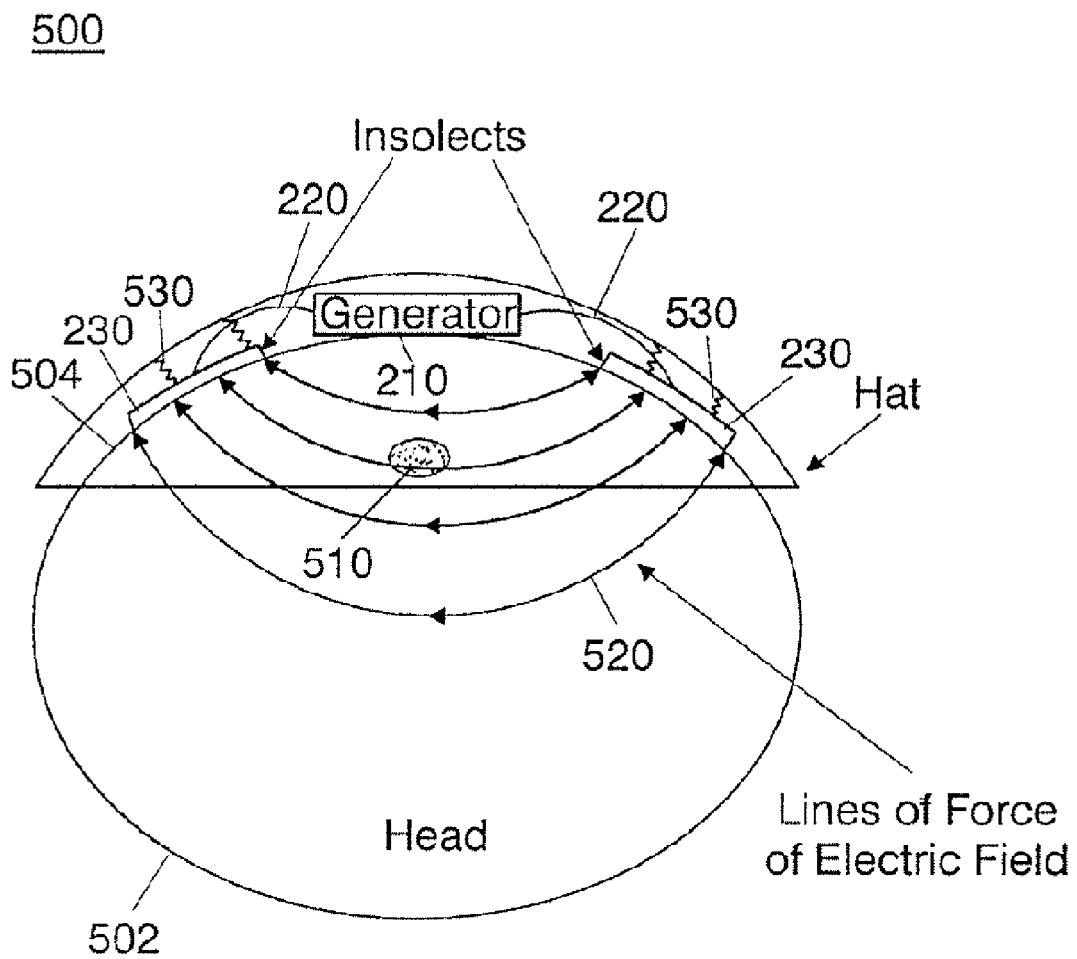

Turning now to FIG. 14 in which an article of clothing 500 according to one exemplary embodiment is illustrated. More specifically, the article of clothing 500 is in the form of a hat or cap or other type of clothing designed for placement on a head of a person. For purposes of illustration, a head 502 is shown with the hat 500 being placed thereon and against a skin surface 504 of the head 502. An intra-cranial tumor or the like 510 is shown as being formed within the head 502 underneath the skin surface 504 thereof. The hat 500 is therefore intended for placement on the head 502 of a person who has a tumor 510 or the like.

Unlike the various embodiments illustrated in FIGS. 1-13 where the insulated electrodes 230 are arranged in a more or less planar arrangement since they are placed either on a skin surface or embedded within the body underneath it, the insulated electrodes 230 in this embodiment are specifically contoured and arranged for a specific application. The treatment of intra-cranial tumors or other lesions or the like typically requires a treatment that is of a relatively long duration, e.g., days to weeks, and therefore, it is desirable to provide as much comfort as possible to the patient. The hat 500 is specifically designed to provide comfort during the lengthy treatment process while not jeopardizing the effectiveness of the treatment.

According to one exemplary embodiment, the hat 500 includes a predetermined number of insulated electrodes 230 that are preferably positioned so as to produce the optimal TC fields at the location of the tumor 510. The lines of force of the TC field are generally indicated at 520. As can be seen in FIG. 14, the tumor 500 is positioned within these lines of force 520. As will be described in greater detail hereinafter, the insulated electrodes 230 are positioned within the hat 500 such that a portion or surface thereof is free to contact the skin surface 504 of the head 502. In other words, when the patient wears the hat 500, the insulated electrodes 230 are placed in contact with the skin surface 504 of the head 502 in positions that are selected so that the TC fields generated thereby are focused at the tumor 510 while leaving surrounding areas in low density. Typically, hair on the head 502 is shaved in selected areas to permit better contact between the insulated electrodes 230 and the skin surface 504; however, this is not critical.

The hat 500 preferably includes a mechanism 530 that applies or force to the insulated electrodes 230 so that they are pressed against the skin surface 502. For example, the mechanism 530 can be of a biasing type that applies a biasing force to the insulated electrodes 230 to cause the insulated electrodes 230 to be directed outwardly away from the hat 500. Thus, when the patient places the hat 500 on his/her head 502, the insulated electrodes 230 are pressed against the skin surface 504 by the mechanism 530. The mechanism 530 can slightly recoil to provide a comfortable fit between the insulated electrodes 230 and the head 502. In one exemplary embodiment, the mechanism 530 is a spring based device that is disposed within the hat 500 and has one section that is coupled to and applies a force against the insulated electrodes 230.

As with the prior embodiments, the insulated electrodes 230 are coupled to the generator 210 by means of conductors 220. The generator 210 can be either disposed within the hat 500 itself so as to provide a compact, self-sufficient, independent system or the generator 210 can be disposed external to the hat 500 with the conductors 220 exiting the hat 500 through openings or the like and then running to the generator 210. When the generator 210 is disposed external to the hat 500, it will be appreciated that the generator 210 can be located in any number of different locations, some of which are in close proximity to the hat 500 itself, while others can be further away from the hat 500. For example, the generator 210 can be disposed within a carrying bag or the like (e.g., a bag that extends around the patient's waist) which is worn by the patient or it can be strapped to an extremity or around the torso of the patient. The generator 210 can also be disposed in a protective case that is secured to or carried by another article of clothing that is worn by the patient. For example, the protective case can be inserted into a pocket of a sweater, etc.

FIG. 14 illustrates an embodiment where the generator 210 is incorporated directly into the hat 500.

Figure 15:
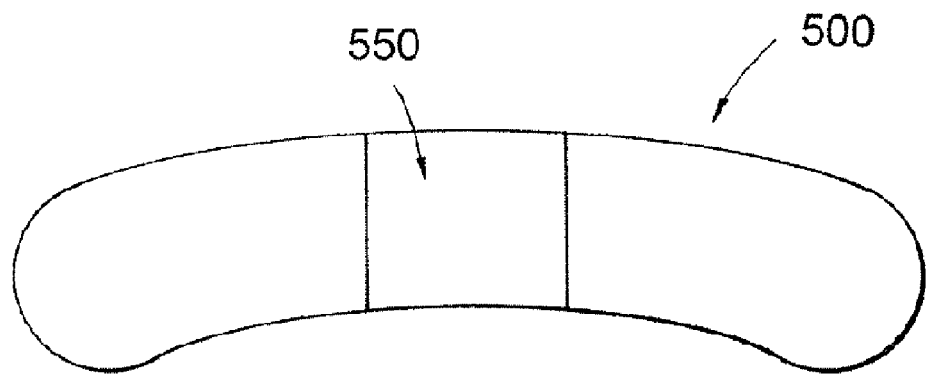
FIG. 15 is a partial section of a hat according to an exemplary embodiment having a recessed section for receiving one or more insulated electrodes.
Figure 16:
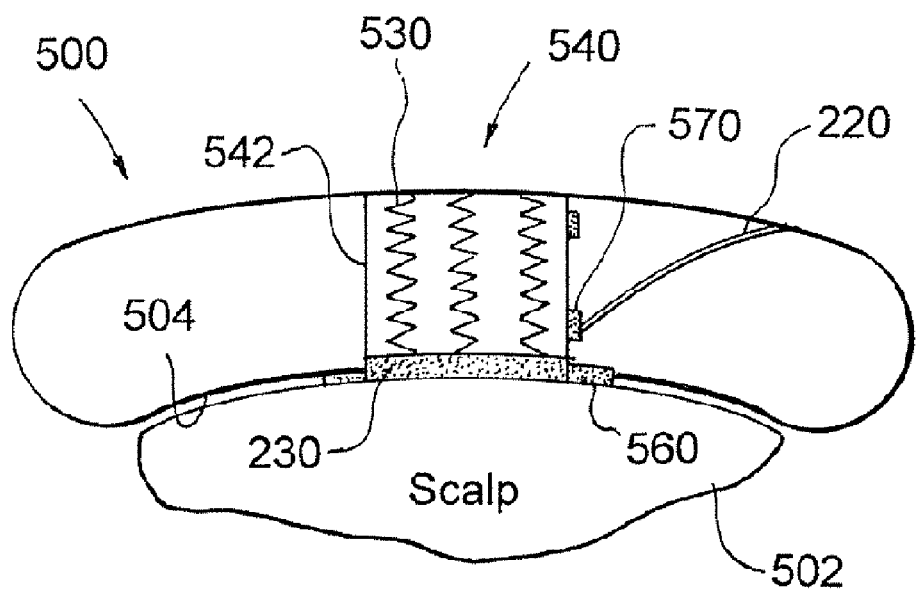
FIG. 16 is a cross-sectional view of the hat of FIG. 15 placed on a head and illustrating a biasing mechanism for applying a force to the insulated electrode to ensure the insulated electrode remains in contact against the head.

Turning now to FIGS. 15 and 16, in one exemplary embodiment, a number of insulated electrodes 230 along with the mechanism 530 are preferably formed as an independent unit, generally indicated at 540, that can be inserted into the hat 500 and electrically connected to the generator (not shown) via the conductors (not shown). By providing these members in the form of an independent unit, the patient can easily insert and/or remove the units 540 from the hat 500 when they may need cleaning, servicing and/or replacement.

In this embodiment, the hat 500 is constructed to include select areas 550 that are formed in the hat 500 to receive and hold the units 540. For example and as illustrated in FIG. 15, each area 550 is in the form of an opening (pore) that is formed within the hat 500. The unit 540 has a body 542 and includes the mechanism 530 and one or more insulated electrodes 230. The mechanism 530 is arranged within the unit 540 so that a portion thereof (e.g., one end thereof) is in contact with a face of each insulated electrode 230 such that the mechanism 530 applies a biasing force against the face of the insulated electrode 230. Once the unit 540 is received within the opening 550, it can be securely retained therein using any number of conventional techniques, including the use of an adhesive material or by using mechanical means. For example, the hat 500 can include pivotable clip members that pivot between an open position in which the opening 550 is free and a closed position in which the pivotable clip members engage portions (e.g., peripheral edges) of the insulated electrodes to retain and hold the insulated electrodes 230 in place. To remove the insulated electrodes 230, the pivotable clip members are moved to the open position. In the embodiment illustrated in FIG. 16, the insulated electrodes 230 are retained within the openings 550 by an adhesive element 560 which in one embodiment is a two sided self-adhesive rim member that extends around the periphery of the insulated electrode 230. In other words, a protective cover of one side of the adhesive rim 560 is removed and it is applied around the periphery of the exposed face of the insulated electrode 230, thereby securely attaching the adhesive rim 560 to the hat 500 and then the other side of the adhesive rim 560 is removed for application to the skin surface 504 in desired locations for positioning and securing the insulated electrode 230 to the head 502 with the tumor being positioned relative thereto for optimization of the TC fields. Since one side of the adhesive rim 560 is in contact with and secured to the skin surface 540, this is why it is desirable for the head 502 to be shaved so that the adhesive rim 560 can be placed fleshly against the skin surface 540.

The adhesive rim 560 is designed to securely attach the unit 540 within the opening 550 in a manner that permits the unit 540 to be easily removed from the hat 500 when necessary and then replaced with another unit 540 or with the same unit 540. As previously mentioned, the unit 540 includes the biasing mechanism 530 for pressing the insulated electrode 230 against the skin surface 504 when the hat 500 is worn. The unit 540 can be constructed so that the side opposite the insulated electrode 230 is a support surface formed of a rigid material, such as plastic, so that the biasing mechanism 530 (e.g., a spring) can be compressed therewith under the application of force and when the spring 530 is in a relaxed state, the spring 530 remains in contact with the support surface and the applies a biasing force at its other end against the insulated electrode 230. The biasing mechanism 530 (e.g., spring) preferably has a contour corresponding to the skin surface 504 so that the insulated electrode 230 has a force applied thereto to permit the insulated electrode 230 to have a contour complementary to the skin surface 504, thereby permitting the two to seat fleshly against one another. While the mechanism 530 can be a spring, there are a number of other embodiments that can be used instead of a spring. For example, the mechanism 530 can be in the form of an elastic material, such as a foam rubber, a foam plastic, or a layer containing air bubbles, etc.

The unit 540 has an electric connector 570 that can be hooked up to a corresponding electric connector, such as a conductor 220, that is disposed within the hat 500. The conductor 220 connects at one end to the unit 540 and at the other end is connected to the generator 210. The generator 210 can be incorporated directly into the hat 500 or the generator 210 can be positioned separately (remotely) on the patient or on a bedside support, etc.

As previously discussed, a coupling agent, such as a conductive gel, is preferably used to ensure that an effective conductive environment is provided between the insulated electrode 230 and the skin surface 504. Suitable gel materials have been disclosed hereinbefore in the discussion of earlier embodiments. The coupling agent is disposed on the insulated electrode 230 and preferably, a uniform layer of the agent is provided along the surface of the electrode 230. One of the reasons that the units 540 need replacement at periodic times is that the coupling agent needs to be replaced and/or replenished. In other words, after a predetermined time period or after a number of uses, the patient removes the units 540 so that the coupling agent can be applied again to the electrode 230.

Figure 17:
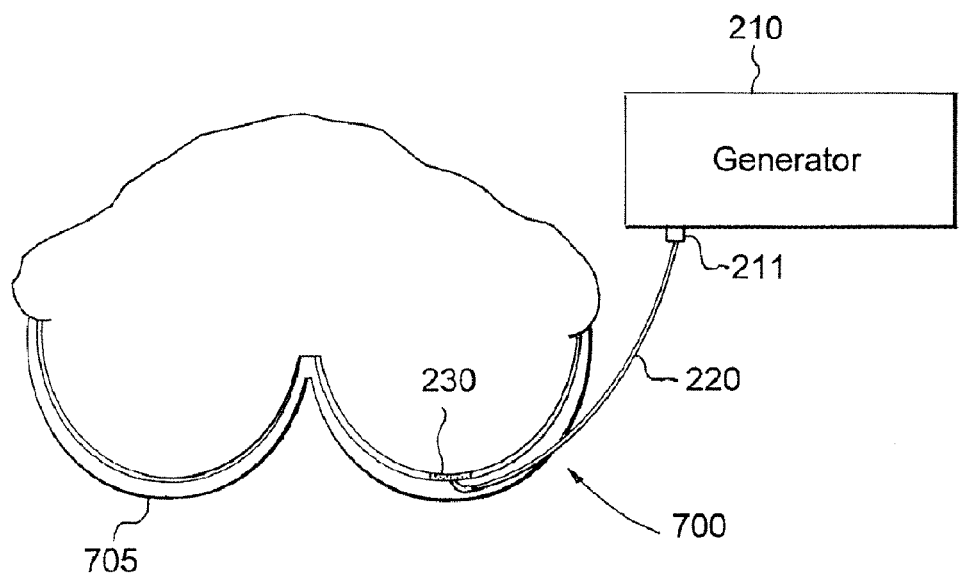
Figure 18:
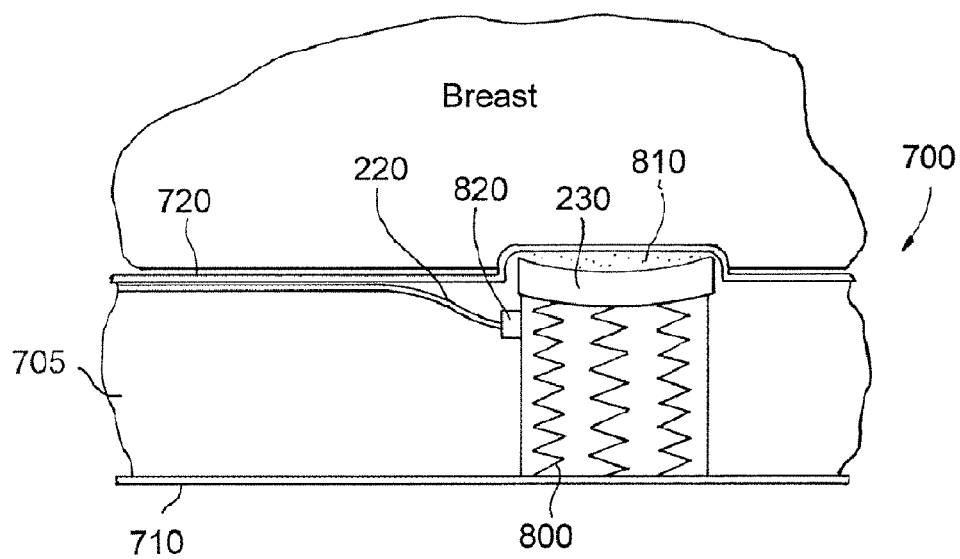
FIG. 18 is a cross-sectional view of a section of the article of clothing of FIG. 17 illustrating a biasing mechanism for biasing the insulated electrode in direction to ensure the insulated electrode is placed proximate to a skin surface where treatment is desired.

FIGS. 17 and 18 illustrate another article of clothing which has the insulated electrodes 230 incorporated as part thereof. More specifically, a bra or the like 700 is illustrated and includes a body that is formed of a traditional bra material, generally indicated at 705, to provide shape, support and comfort to the wearer. The bra 700 also includes a fabric support layer 710 on one side thereof. The support layer 710 is preferably formed of a suitable fabric material that is constructed to provide necessary and desired support to the bra 700.

Similar to the other embodiments, the bra 700 includes one or more insulated electrodes 230 disposed within the bra material 705. The one or more insulated electrodes are disposed along an inner surface of the bra 700 opposite the support 710 and are intended to be placed proximate to a tumor or the like that is located within one breast or in the immediately surrounding area. As with the previous embodiment, the insulated electrodes 230 in this embodiment are specifically constructed and configured for application to a breast or the immediate area. Thus, the insulated electrodes 230 used in this application do not have a planar surface construction but rather have an arcuate shape that is complementary to the general curvature found in a typical breast.

A lining 720 is disposed across the insulated electrodes 230 so as to assist in retaining the insulated electrodes in their desired locations along the inner surface for placement against the breast itself. The lining 720 can be formed of any number of thin materials that are comfortable to wear against one's skin and in one exemplary embodiment, the lining 720 is formed of a fabric material.

The bra 700 also preferably includes a biasing mechanism 800 as in some of the earlier embodiments. The biasing mechanism 800 is disposed within the bra material 705 and extends from the support 710 to the insulated electrode 230 and applies a biasing force to the insulated electrode 230 so that the electrode 230 is pressed against the breast. This ensures that the insulated electrode 230 remains in contact with the skin surface as opposed to lifting away from the skin surface, thereby creating a gap that results in a less effective treatment since the gap diminishes the efficiency of the TC fields. The biasing mechanism 800 can be in the form of a spring arrangement or it can be an elastic material that applies the desired biasing force to the insulated electrodes 230 so as to press the insulated electrodes 230 into the breast. In the relaxed position, the biasing mechanism 800 applies a force against the insulated electrodes 230 and when the patient places the bra 700 on their body, the insulated electrodes 230 are placed against the breast which itself applies a force that counters the biasing force, thereby resulting in the insulated electrodes 230 being pressed against the patient's breast. In the exemplary embodiment that is illustrated, the biasing mechanism 800 is in the form of springs that are disposed within the bra material 705.

A conductive gel 810 can be provided on the insulated electrode 230 between the electrode and the lining 720. The conductive gel layer 810 is formed of materials that have been previously described herein for performing the functions described above.

An electric connector 820 is provided as part of the insulated electrode 230 and electrically connects to the conductor 220 at one end thereof, with the other end of the conductor 220 being electrically connected to the generator 210. In this embodiment, the conductor 220 runs within the bra material 705 to a location where an opening is formed in the bra 700. The conductor 220 extends through this opening and is routed to the generator 210, which in this embodiment is disposed in a location remote from the bra 700. It will also be appreciated that the generator 210 can be disposed within the bra 700 itself in another embodiment. For example, the bra 700 can have a compartment formed therein which is configured to receive and hold the generator 210 in place as the patient wears the bra 700. In this arrangement, the compartment can be covered with a releasable strap that can open and close to permit the generator 210 to be inserted therein or removed therefrom. The strap can be formed of the same material that is used to construct the bra 700 or it can be formed of some other type of material. The strap can be releasably attached to the surrounding bra body by fastening means, such as a hook and loop material, thereby permitting the patient to easily open the compartment by separating the hook and loop elements to gain access to the compartment for either inserting or removing the generator 210.

The generator 210 also has a connector 211 for electrical connection to the conductor 220 and this permits the generator 210 to be electrically connected to the insulated electrodes 230.

As with the other embodiments, the insulated electrodes 230 are arranged in the bra 700 to focus the electric field (TC fields) on the desired target (e.g., a tumor). It will be appreciated that the location of the insulated electrodes 230 within the bra 700 will vary depending upon the location of the tumor. In other words, after the tumor has been located, the physician will then devise an arrangement of insulated electrodes 230 and the bra 700 is constructed in view of this arrangement so as to optimize the effects of the TC fields on the target area (tumor). The number and position of the insulated electrodes 230 will therefore depend upon the precise location of the tumor or other target area that is being treated. Because the location of the insulated electrodes 230 on the bra 700 can vary depending upon the precise application, the exact size and shape of the insulated electrodes 230 can likewise vary. For example, if the insulated electrodes 230 are placed on the bottom section of the bra 700 as opposed to a more central location, the insulated electrodes 230 will have different shapes since the shape of the breast (as well as the bra) differs in these areas.

Figure 19:
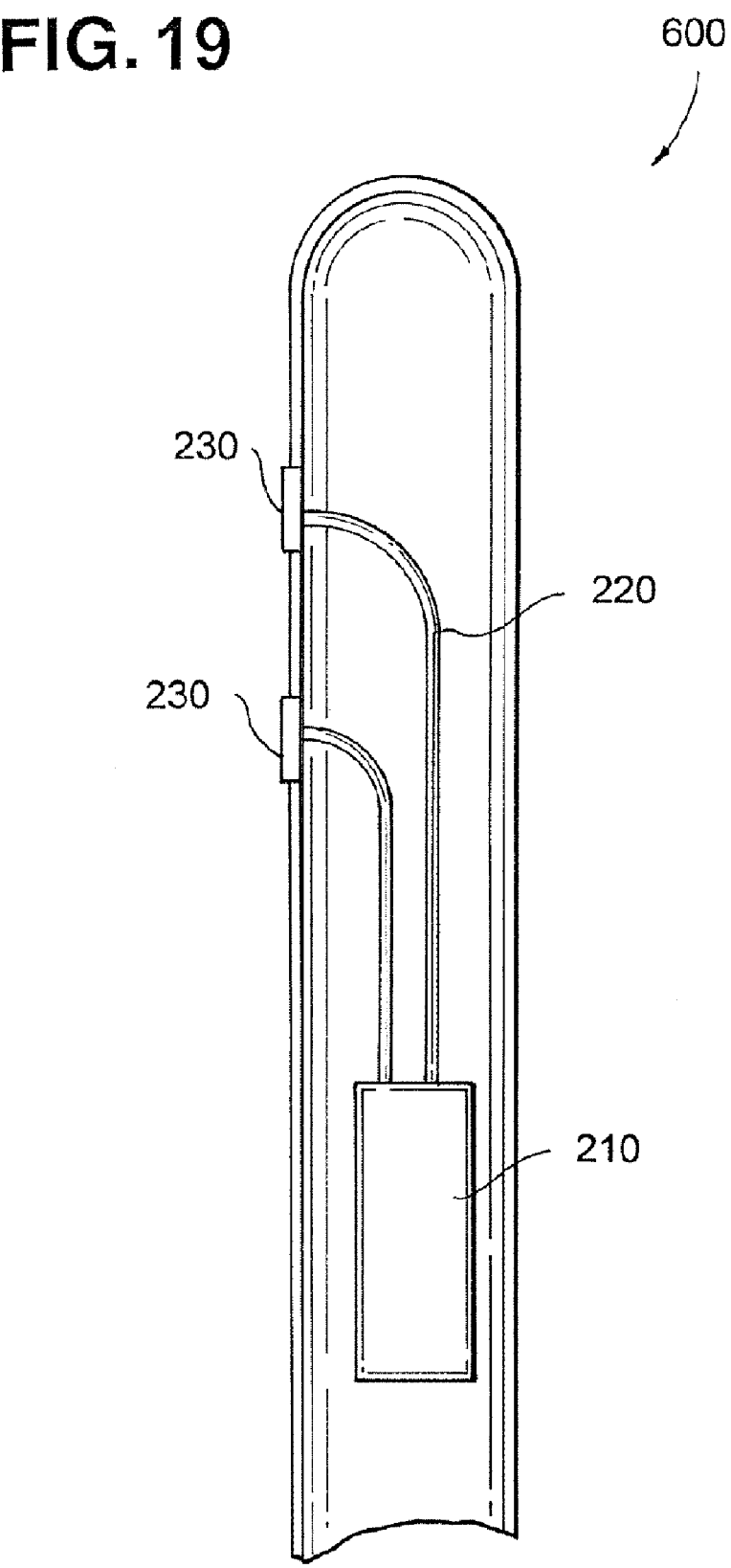

FIG. 19 illustrates yet another embodiment in which the insulated electrodes 230 are in the form of internal electrodes that are incorporated into in the form of a probe or catheter 600 that is configured to enter the body through a natural pathway, such as the urethra, vagina, etc. In this embodiment, the insulated electrodes 230 are disposed on an outer surface of the probe 600 and along a length thereof. The conductors 220 are electrically connected to the electrodes 230 and run within the body of the probe 600 to the generator 210 which can be disposed within the probe body or the generator 210 can be disposed independent of the probe 600 in a remote location, such as on the patient or at some other location close to the patient.

Alternatively, the probe 600 can be configured to penetrate the skin surface or other tissue to reach an internal target that lies within the body. For example, the probe 600 can penetrate the skin surface and then be positioned adjacent to or proximate to a tumor that is located within the body.

In these embodiments, the probe 600 is inserted through the natural pathway and then is positioned in a desired location so that the insulated electrodes 230 are disposed near the target area (i.e., the tumor). The generator 210 is then activated to cause the insulated electrodes 230 to generate the TC fields which are applied to the tumor for a predetermined length of time. It will be appreciated that the illustrated probe 600 is merely exemplary in nature and that the probe 600 can have other shapes and configurations so long as they can perform the intended function. Preferably, the conductors (e.g., wires) leading from the insulated electrodes 230 to the generator 210 are twisted or shielded so as not to generate a field along the shaft.

Figure 20:
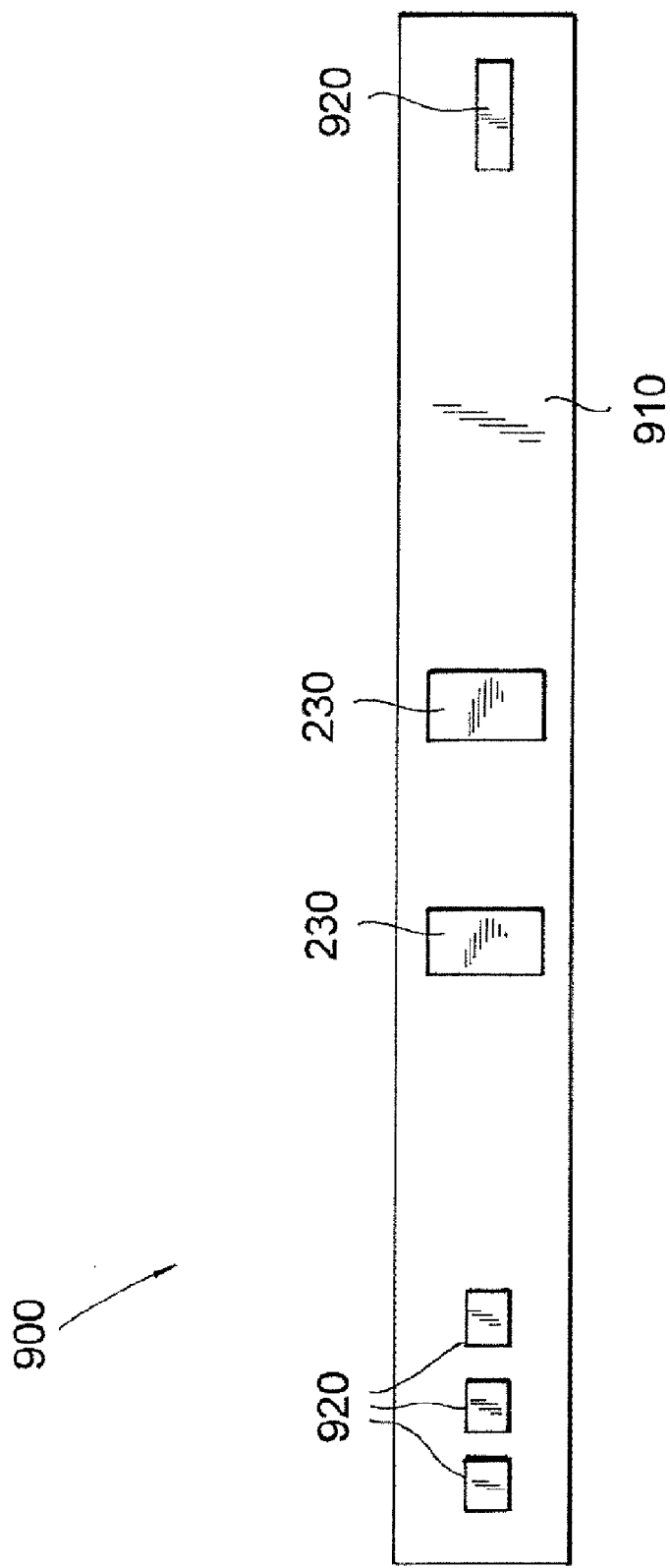
FIG. 20 is an elevational view of an unwrapped collar according to one exemplary embodiment for placement around a neck for treating a tumor or the like in this area when the collar is wrapped around the neck.

FIG. 20 illustrates yet another embodiment in which a high standing collar member 900 (or necklace type structure) can be used to treat thyroid, parathyroid, laryngeal lesions, etc. FIG. 20 illustrates the collar member 900 in an unwrapped, substantially flat condition. In this embodiment, the insulated electrodes 230 are incorporated into a body 910 of the collar member 900 and are configured for placement against a neck area of the wearer. The insulated electrodes 230 are coupled to the generator 210 according to any of the manner described hereinbefore and it will be appreciated that the generator 210 can be disposed within the body 910 or it can be disposed in a location external to the body 910. The collar body 910 can be formed of any number of materials that are traditionally used to form collars 900 that are disposed around a person's neck. As such, the collar 900 preferably includes a means 920 for adjusting the collar 900 relative to the neck. For example, complementary fasteners (hook and loop fasteners, buttons, etc.) can be disposed on ends of the collar 900 to permit adjustment of the collar diameter.

Thus, the construction of the present devices are particularly well suited for applications where the devices are incorporated into articles of clothing to permit the patient to easily wear a traditional article of clothing while at the same time the patient undergoes treatment. In other words, an extra level of comfort can be provided to the patient and the effectiveness of the treatment can be increased by incorporating some or all of the device components into the article of clothing. The precise article of clothing that the components are incorporated into will obviously vary depending upon the target area of the living tissue where tumor, lesion or the like exists. For example, if the target area is in the testicle area of a male patient, then an article of clothing in the form of a sock-like structure or wrap can be provided and is configured to be worn around the testicle area of the patient in such a manner that the insulated electrodes thereof are positioned relative to the tumor such that the TC fields are directed at the target tissue. The precise nature or form of the article of clothing can vary greatly since the device components can be incorporated into most types of articles of clothing and therefore, can be used to treat any number of different areas of the patient's body where a condition may be present.

While the invention has been particularly shown and described with reference to preferred embodiments thereof, it will be understood by those skilled in the art that various changes in form and details can be made without departing from the spirit and scope of the invention.

What is claimed is:

1. An apparatus for selectively destroying dividing cells in a target area of living tissue, the dividing cells having members with strong dipole moments, the apparatus comprising:
    an article of clothing constructed to be worn over the target area;
    a first insulated electrode having a first conductor and a first dielectric coating, wherein the first insulated electrode is affixed to the article of clothing so that when the article of clothing is worn by a person, the first dielectric coating is positioned between the first conductor and the person's body and is held against the person's body;
    a second insulated electrode having a second conductor and a second dielectric coating, wherein the second insulated electrode is affixed to the article of clothing so that when the article of clothing is worn by the person, the second dielectric coating is positioned between the second conductor and the person's body and is held against the person's body; and
    an electric potential source configured to impose an alternating electric potential across the first and second conductors, wherein the alternating electric potential and the insulated electrodes are configured to operate together to impose, in the target area, an electric field with frequency and amplitude characteristics such that application of the electric field to the dividing cells in late anaphase or telophase gives rise to a non-homogenous electric field within the dividing cells that causes the members with strong dipole moments within the dividing cells to move in a manner that increases the likelihood that the dividing cells will structurally break apart.

2. The apparatus of claim 1, wherein the non-homogenous field causes the members with strong dipole moments to move towards a region of a cleavage furrow of the dividing cells.

3. The apparatus of claim 1, wherein each insulated electrode includes a dielectric layer adjacent the conductor and for placement against the living tissue.

4. The apparatus of claim 3, wherein the dielectric layer is formed of a material having a high dielectric constant and is selected from the group consisting of lithium nibate (LiNbO3); yttrium iron garnet (YIG); barium titanate (BaTiO3); potassium tantalate (kTaO3); and lithium tantalate (LiTaO3).

5. The apparatus of claim 3 wherein the article of clothing is selected from the group consisting of: a hat, a bra, a neck collar, and an undergarment.

6. The apparatus of claim 3 wherein the frequency of the imposed electric field is between 100 kHz and 300 kHz.

7. The apparatus of claim 3 wherein the intensity of the imposed electric field is between 0.1 V/cm and 10 V/cm.

8. The apparatus of claim 1 wherein the frequency of the imposed electric field is between 100 kHz and 300 kHz and the intensity of the imposed electric field is between 0.1 V/cm and 10 V/cm.

9. A method for selectively destroying dividing cells in a target area of living tissue, the dividing cells having members with strong dipole moments, the method comprising:
    holding a first insulated electrode having a first conductor and a first dielectric coating against a person's body using an article of clothing, with the first dielectric coating positioned between the first conductor and the person's body;
    holding a second insulated electrode having a second conductor and a second dielectric coating against a person's body using the article of clothing, with the second dielectric coating positioned between the second conductor and the person's body; and
    imposing an alternating electric potential across the first and second conductors, wherein the alternating electric potential and the insulated electrodes are configured to operate together to impose, in the target area, an electric field with frequency and amplitude characteristics such that application of the electric field to the dividing cells in late anaphase or telophase gives rise to a non-homogenous electric field within the dividing cells that causes the members with strong dipole moments within the dividing cells to move in a manner that increases the likelihood that the dividing cells will structurally break apart.

10. The method of claim 9, wherein the non-homogenous field causes the members with strong dipole moments to move towards a region of a cleavage furrow of the dividing cells.

11. The method of claim 9, wherein each insulated electrode includes a dielectric layer adjacent the conductor and for placement against the living tissue.

12. The method of claim 11, wherein the dielectric layer is formed of a material having a high dielectric constant and is selected from the group consisting of lithium nibate (LiNbO3); yttrium iron garnet (YIG); barium titanate (BaTiO3); potassium tantalate (kTaO3); and lithium tantalate (LiTaO3).

13. The method of claim 11, wherein the article of clothing is selected from the group consisting of: a hat, a bra, a neck collar, and an undergarment.

14. The apparatus of claim 11, wherein the frequency of the imposed electric field is between 100 kHz and 300 kHz.

15. The method of claim 11, wherein the intensity of the imposed electric field is between 0.1 V/cm and 10 V/cm.

16. The method of claim 9, wherein the frequency of the imposed electric field is between 100 kHz and 300 kHz and the intensity of the imposed electric field is between 0.1 V/cm and 10 V/cm.

* * * * *